US008980248B2

(12) United States Patent
Shoichet et al.

(10) Patent No.: US 8,980,248 B2
(45) Date of Patent: Mar. 17, 2015

(54) INJECTABLE POLYMER COMPOSITION FOR USE AS A CELL DELIVERY VEHICLE

(75) Inventors: Molly Sandra Shoichet, Toronto (CA); Tasneem Zahir, Mississauga (CA); Brian Ballios, Mississauga (CA); Derek Van der Kooy, Toronto (CA); Michael Cooke, Toronto (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 0 days.

(21) Appl. No.: 13/516,846

(22) PCT Filed: Dec. 17, 2010

(86) PCT No.: PCT/CA2010/002060
§ 371 (c)(1),
(2), (4) Date: Oct. 16, 2012

(87) PCT Pub. No.: WO2011/072399
PCT Pub. Date: Jun. 23, 2011

(65) Prior Publication Data
US 2013/0189230 A1    Jul. 25, 2013

Related U.S. Application Data

(60) Provisional application No. 61/288,043, filed on Dec. 18, 2009.

(51) Int. Cl.
| A61K 47/48 | (2006.01) |
| A61K 9/00 | (2006.01) |
| A61K 47/36 | (2006.01) |
| A61K 47/38 | (2006.01) |
| A61L 27/16 | (2006.01) |
| A61L 27/20 | (2006.01) |

(52) U.S. Cl.
CPC ......... *A61K 47/48169* (2013.01); *A61K 9/0024* (2013.01); *A61K 47/36* (2013.01); *A61K 47/38* (2013.01); *A61L 27/16* (2013.01); *A61L 27/20* (2013.01); *A61K 47/4823* (2013.01); *A61L 2300/62* (2013.01); *A61L 2300/64* (2013.01); *A61L 2400/06* (2013.01)
USPC ......................................... 424/93.7; 514/781

(58) Field of Classification Search
CPC . A61K 47/48169; A61K 47/36; A61K 47/38; A61K 9/0024; A61K 47/4823; A61L 27/16; A61L 27/20; A61L 2400/06; A61L 2300/64; A61L 2300/62
USPC ........................................ 424/93.7; 514/781
See application file for complete search history.

(56) References Cited

U.S. PATENT DOCUMENTS

| 4,065,578 | A | 12/1977 | Reggio et al. |
| 4,140,562 | A | 2/1979 | Gualillo et al. |
| 4,786,521 | A | 11/1988 | Bennett et al. |
| 5,153,174 | A | 10/1992 | Band et al. |
| 5,190,759 | A | 3/1993 | Lindblad et al. |
| 5,607,999 | A | 3/1997 | Shimizu et al. |
| 5,622,718 | A | 4/1997 | Al-Shamkhani et al. |
| 5,651,980 | A | 7/1997 | Lanza et al. |
| 5,997,895 | A | 12/1999 | Narotam et al. |
| 6,063,405 | A | 5/2000 | Drizen et al. |
| 6,335,035 | B1 | 1/2002 | Drizen et al. |
| 6,440,940 | B1 | 8/2002 | Doyle et al. |
| 6,548,081 | B2 | 4/2003 | Sadozai et al. |
| 6,586,493 | B1 | 7/2003 | Massia et al. |
| 6,602,859 | B2 | 8/2003 | Miyamoto et al. |
| 6,620,927 | B2 | 9/2003 | Bulpitt et al. |
| 6,642,213 | B1 | 11/2003 | Pastorello et al. |
| 6,692,766 | B1 | 2/2004 | Rubinstein et al. |
| 6,699,471 | B2 | 3/2004 | Radice et al. |
| 6,699,484 | B2 | 3/2004 | Whitmore et al. |
| 6,716,251 | B1 | 4/2004 | Asius et al. |
| 7,767,656 | B2 * | 8/2010 | Shoichet et al. ............... 514/57 |
| 2004/0191225 | A1 * | 9/2004 | Dinsmore et al. ........... 424/93.7 |
| 2006/0280797 | A1 * | 12/2006 | Shoichet et al. ............. 424/486 |
| 2007/0037737 | A1 * | 2/2007 | Hoemann et al. ............... 514/8 |

(Continued)

FOREIGN PATENT DOCUMENTS

| CA | 2 379 971 | A1 | | 4/2001 |
| CN | 101695584 | A | | 4/2010 |
| JP | 2003-342197 | A | | 12/2003 |
| KR | 20090061745 | A | | 6/2009 |
| WO | WO0124842 | | * | 4/2001 |

OTHER PUBLICATIONS

Ballios, Brian G. et al., "A hydrogel-based stem cell delivery system to treat retinal degenerative diseases", Biomaterials, 31: 2555-2564 (2010).

(Continued)

*Primary Examiner* — Karen Cochrane Carlson
*Assistant Examiner* — Jennifer M. H. Tichy
(74) *Attorney, Agent, or Firm* — Dann, Dorfman, Herrell and Skillman, P.C.; Patrick J. Hagan

(57) ABSTRACT

This invention provides a polymer composition comprising at least one thermal gelling polymer and at least one anionic polymer for cell delivery applications. These injectable polymer compositions are shear-thinning, thixotropic and resorbable. More specifically there is described a hyaluronan (HA) and methylcellulose (MC) based thermogelling cell delivery system (HAMC) that promotes cell survival both in vitro and in vivo. Importantly, HAMC (relative to media alone) enhances survival of transplanted stem/progenitor cells in the injured CNS. HAMC provides a minimally-invasive cell delivery strategy where the microenvironment can be further defined and the differentiation and regenerative capacity further explored. This hydrogel system has applications for minimally-invasive cell delivery to other tissues/organs in the body as well.

16 Claims, 20 Drawing Sheets

(56) References Cited

U.S. PATENT DOCUMENTS

| | | | |
|---|---|---|---|
| 2007/0104695 A1* | 5/2007 | Quijano et al. | 424/93.7 |
| 2007/0224174 A1* | 9/2007 | Kang et al. | 424/93.7 |
| 2008/0187524 A1* | 8/2008 | Fernandes et al. | 424/93.21 |
| 2008/0226692 A1* | 9/2008 | Sato et al. | 424/424 |
| 2009/0220464 A1* | 9/2009 | Aggarwal et al. | 424/93.7 |

OTHER PUBLICATIONS

Basso, D. Michele, "Graded Histological and Locomotor Outcomes after Spinal Cord Contusion Using the NYU Weight-Drop Device versus Transection", Experimental Neurology, 139: 244-256 (1996).

Baumann, M. Douglas et al., "An injectable drug delivery platform for sustained combination therapy", J. Controlled Release, 138: 205-213 (2009).

Chenite, A. et al., "Novel injectable neutral soloutions of chitosan form biodegradable gels in situ", Biomaterials, 21: 2155-2161 (2000).

Cho, K.Y. et al., "Release of ciprofloxacin from poloxamer-graft-hyaluronic acid hydrogels in vitro", Int. J. Pharmac., 260: 83-91 (2003).

Hoffman, Allan S., "Bioconjugates of Intelligent Polymers and Recognition Proteins for Use in Diagnostics and Affinity Separations", Clinical Chemistry, 46: 1478-1486 (2000).

Kim, Mee Ryang et al., "Temperature-responsive and degradable hyaluronic acid/Pluronic composite hydrogels for controlled release of human growth hormone", J. Controlled Release, 80: 69-77 (2002).

Larson, Ronald G., "The rheology of dilute solutions of flexible polymers: progress and problems", J. Rheology, 49 (1): 1-70 (2005).

Liang, Hsiang-Fa et al., "Novel Method Using a Temperature-Sensitive Polymer (Methylcellulose) to Thermally Gel Aqueous Alginate as a pH-Sensitive Hydrogel", Biomacromolecules, 5: 1917-1925 (2004).

Metz, Gerlinde A.S. et al., "Efficient testing of motor function in spinal cord injured rats", Brain Research, 883: 165-177 (2000).

Ohya, Shoji et al., "Thermoresponsive Artificial Extracellular Matrix for Tissue Engineering: Hyaluronic Acid Bioconjugated with Poly(N-isopropylacrylamide) Grafts", Biomacromolecules, 2: 856-863 (2001).

Prestwich, Glenn D. et al., "Controlled chemical modification of hyaluronic acid: synthesis, applications, and biodegradation of hydrazide derivatives", J. Controlled Release, 53: 93-103 (1998).

Sakiyama-Elbert, Shelly et al., "Development of fibrin derivatives for controlled release of heparin-binding growth factors", J. Controlled Release, 65: 389-402 (2000).

Shoichet, Molly S. et al., "Intrathecal drug delivery strategy is safe and efficacious for localized delivery to the spinal cord", Progress in Brain Research, 61: 385-392 (2007).

Silver, Frederick H., "Physical Properties of Hyaluronic Acid and Hydroxypropylmethylcellulose in Solution: Evaluation of Coating Ability", J. App. Biomaterials, 5: 89-98 (194).

Tate, Matthew C., "Biocompatibility of methylcellulose-based constructs designed for intracerebral gelation following experimental traumatic brain injury", Biomaterials, 22: 1113-1123 (2001).

Xu, Y. et al., "Salt-Assisted and Salt-Suppressed Sol-gel Transitions of Methylcellulose in Water", Langmuir, 20: 646-652 (2004).

International Search Report/Written Opinion, issued Mar. 25, 2011, from corresponding International Application No. PCT/CA2010/002060.

* cited by examiner (open circles are HA; closed circles are MC)

| Amino acid | pmol/μL (0.46mg/mL sample) |
|---|---|
| Asp | 65.84 |
| Ser | 74.74 |
| Gly | 163.19 |
| Arg | 76.21 |
| AVG | 75.99 |
| Std. Dev. | 6.47 |
| % RSD | 8.51 |
| Response factor | 0.6455 |

INJECTABLE POLYMER COMPOSITION FOR USE AS A CELL DELIVERY VEHICLE

CROSS-REFERENCE TO RELATED APPLICATIONS

This application is the U.S. National Stage of International Application No. PCT/CA2010/002060, filed Dec. 17, 2010, which claims the benefit of U.S. Provisional Patent Application No. 61/288,043, filed Dec. 18, 2009. The entire disclosure of each of the aforesaid applications is incorporated by reference in the present application.

FIELD

An injectable polymer composition for use as a cell delivery vehicle comprising at least one thermal gelling polymer; at least one anionic gelling polymer; a water-based carrier, wherein the polymer composition is injectable due to its shear thinning properties.

BACKGROUND

Various publications, including patents, published applications, technical articles and scholarly articles are cited throughout the specification. Each of these cited publications is incorporated by reference herein, in its entirety.

While cell transplantation is a promising therapy to overcome injury and disease, the widespread application of this approach is limited by the poor survival, differentiation, and integration of cells transplanted into a site of injury. Injectable, bioresorbable hydrogels present a viable approach to overcome the barriers of cell survival and integration. Unlike pre-formed tissue-engineered scaffolds that generally require invasive surgical techniques for implantation, injectable hydrogels offer the potential of minimally invasive cell delivery through a needle or catheter into a cavity that results from tissue loss due to disease, aging or injury, or into the healthy tissue near the diseased or injured or aged tissue. The gel could conform to the shape of the lesion cavity if injected therein where it could also serve as a "bridge" across which regeneration may occur. Most of the hydrogel systems developed to date have been designed for the delivery of therapeutic molecules. This is especially true to the injured or diseased central nervous system (CNS), where neurotrophic factors [Tomita M, Lavik E, Klassen H, Zahir T, Langer R, Young M J. *Biodegradable polymer composite grafts promote the survival and differentiation of retinal progenitor cells. Stem Cells* 2005; 23:1579-88; Lavik E B, Klassen H, Warfvinge K, Langer R, Young M J. *Fabrication of degradable polymer scaffolds to direct the integration and differentiation of retinal progenitors. Biomaterials* 2005; 26:3187-96; Kubitz J C, Motsch J. *Eye surgery in the elderly. Best Pract Res Clin Anaesthesiol* 2003; 17:245-57; Tschon M, Fini M, Giavaresi G, Torricelli P, Rimondini L, Ambrosio L et al. *In vitro and in vivo behaviour of biodegradable and injectable PLA/PGA copolymers related to different matrices. Int J Artif Organs* 2007; 30:352-62], neuroprotective molecules [Wallace D G, Rosenblatt J. *Collagen gel systems for sustained delivery and tissue engineering. Advanced Drug Delivery Reviews* 2003; 55:1631-49], and antibodies against axonal regeneration inhibitors [Chemte A, Chaput C, Wang D, Combes C, Buschmann M D, Hoemann C D et al. *Novel injectable neutral solutions of chitosan form biodegradable gels in situ. Biomaterials* 2000; 21:2155-61] have been delivered. The necessity to enhance the survival of transplanted cells (primary, cell lines, stem/progenitor or precursor cells) in vivo requires a delivery vehicle. This is important to numerous diseases and injuries, including diabetes, heart-related conditions, arthritis (osteo and rheumatoid), joint injuries, CNS diseases and disorders including retinitis pigmentosa, age-related macular degeneration, Parkinson's disease, Huntington's disease, Alzheimer's disease, multiple sclerosis, amyotrophic lateral sclerosis, spinal muscular atrophy, age-related macular degeneration, stroke, cerebral palsy, and spinal cord injury.

Diseases of the retina and retinal function can lead to permanent loss of visual function for which there is no definitive treatment. The detrimental impact of vision loss on quality of life and activities of daily living has been well documented and affects the entire age spectrum. Retinitis pigmentosa (RP) affects the pediatric and young adult population, and is the leading cause of inherited retinal degeneration-associated blindness [Shintani K, Shechtman D L, Durwood A S. *Review and update: Current treatment trends for patients with retinitis pigmentosa. Optometry* 2009; 80:384-401]. Diabetic retinopathy is the principle cause of blindness in middle-aged working adults [Klein B E K. *Overview of epidemiologic studies of diabetic retinopathy. Ophthalmic Epidemiol* 2007; 14:179-83]. Age-related macular degeneration (AMD) is the leading cause of irreversible blindness and moderate visual impairment in developed nations: there are an estimated 200,000 new cases annually in the United States [Kaufman S R. *Developments in age-related macular degeneration: Diagnosis and treatment. Geriatrics* 2009; 64:16-19]. Irreversible photoreceptor death or loss of function is common to all of these pathologies. It is expected that rates of blindness due to retinal degeneration will rise as our population ages in the coming decades [Congdon N G, Friedman D S, Lietman T. *Important Causes of Visual Impairment in the World Today. J Am Med Assoc* 2003; 290:2057-6; Lee P, Wang C C, Adamis A P. *Ocular neovascularization: An epidemiologic review. Surv Ophthalmol* 1998; 43:245-69], providing a strong impetus in the search for new therapies.

Current therapies for vision loss have focused predominantly on pharmacological treatments. For example, there have been recent advances in the treatment of the neovascular (wet) form of AMD with anti-vascular endothelial growth factor therapies [Rosenfeld P J, Brown D M, Heier J S, Boyer D S, Kaiser P K, Chung C Y et al. *Ranibizumab for neovascular age-related macular degeneration. N Engl J Med* 2006; 355:1419-31; Menon G, Walters G. *New paradigms in the treatment of wet AMD: The impact of anti-VEGF therapy. Eye* 2009; 23(suppl. 1):S1-7]. Experimental treatments of diabetic retinopathy focus on bioactive molecules such as advanced glycosylation end product inhibitors and anti-oxidants to counter oxygen-induced injury [Corner G M, Ciulla T A. *Current and future pharmacological intervention for diabetic retinopathy. Expert Opin Emerg Drugs* 2005; 10:441-55]. While these therapies show promise in limiting the pathophysiologic advancement of the disease, they do not represent a restorative approach.

Cellular transplantation therapy is an alternate strategy in which auto- or allogenic cellular material is used to replenish damaged retinal cells. The inner retinal microstructure in both AMD and RP is relatively intact following pathological photoreceptor degeneration, and one regenerative approach is to repopulate these cells without having to recapitulate the intricate retinal architecture. Various types of retinal tissue have now been allografted in the treatment of retinal disease: fetal retinal pigmented epithelium (RPE) cells to patients with AMD [(9) Algvere P V, Gouras P, Kopp E D. *Long-term outcome of RPE allografts in nonimmunosuppressed patients with AMD. Eur J Ophthalmol* 1999; 9:217-30; Algvere P V, Berglin L, Gouras P, Sheng Y. *Human fetal RPE transplants in*

Age Related Macular Degeneration (ARMD). Invest Ophthalmol Vis Sci 1996; 37:S96], and neural retinal cells to patients with RP [Das T P, Del Cerro M, Lazar E S, Jalali S, DiLoreto D A, Little C W et al. *Transplantation of neural retina in patients with retinitis pigmentosa. Invest Ophthalmol V is Sci* 1996; 37:S96]. Treating AMD by targeting RPE regeneration or transplantation is a therapeutically relevant option being pursued through research [Chen F K, Uppal G S, Maclaren R E, Coffey P J, Rubin G S, Tufail A et al. *Long-term visual and microperimetry outcomes following autologous retinal pigment epithelium choroid graft for neovascular age-related macular degeneration. Clin Experiment Ophthalmol* 2009; 37:275-85; Da Cruz L, Chen F K, Ahmado A, Greenwood J, Coffey P. *RPE transplantation and its role in retinal disease. Prog Retin Eye Res* 2007; 26:598-635]. While graft survival is observed in some cases, improvements in visual acuity are disappointing to date [Berson E L, Jakobiec F A. *Neural retinal cell transplantation: Ideal versus reality. Ophthalmology* 1999; 106:445-46].

Experimental research suggests that stem cell transplantation shows promise for reconstituting the damaged cellular populations of the retina [Klassen H, Sakaguchi D S, Young M J. *Stem cells and retinal repair. Prog Retin Eye Res* 2004; 23:149-81; Enzmann V, Yolcu E, Kaplan H J, Ildstad S T. *Stem cells as tools in regenerative therapy for retinal degeneration. Arch Ophthalmol* 2009; 127:563-71]. One of the key advantages of using stem cells is their potential to differentiate into any type of cell, including retinal neurons and RPE [Das A M, Zhao X Ahmad I. *Stem cell therapy for retinal degeneration: Retinal neurons from heterologous sources. Semin Ophthalmol* 2005; 20:3-10]. For cell replacement therapy in the retina, the discovery of adult retinal stem cells (RSCs) [Tropepe V, Coles B L K, Chiasson B J, Horsford D J, Elia A J, McInnes R R et al. *Retinal stem cells in the adult mammalian eye. Science* 2000; 287:2032-36] and their isolation in humans [Coles B L K, Angenieux B, Inoue T, Rio-Tsonis K, Spence J R, McInnes R R et al. *Facile isolation and the characterization of human retinal stem cells. Proc Natl Acad Sci USA* 2004; 101:15772-7] was a major step forward, avoiding the ethical concerns regarding the use of embryonic/fetal tissue [Sugarman J. *Human Stem Cell Ethics: Beyond the Embryo. Cell Stem Cell* 2008; 2:529-33]. It has been shown that cells derived from the pigmented ciliary margin can give rise to all retinal cell types as well as can integrate into the retinae of early postnatal mice [Coles B L K, Angenieux B, Inoue T, Rio-Tsonis K, Spence J R, McInnes R R et al. *Facile isolation and the characterization of human retinal stem cells. Proc Natl Acad Sci USA* 2004; 101:15772-7]. The developing mouse eye is a permissive environment for cellular integration due to the presence of differentiation and proliferation signals and the absence of a mature glial limitans membrane, which prevents transplanted cells from migrating into the neural retina in adult intravitreal cellular transplantation [Kinouchi R, Takeda M, Yang L, Wilhelmsson U, Lundkvist A, Pekny M et al. *Robust neural integration from retinal transplants in mice deficient in GFAP and vimentin. Nat Neurosci* 2003; 6:863-8]. To bypass this membrane in adults, the target for cellular replacement therapy is subretinal. Barriers to adult subretinal transplantation include cellular survival and host tissue integration. It has been well documented that cell death, leakage and migration from the injection site occurs when retinal progenitor cells are delivered as a single cell suspension in saline [Klassen H J, Ng T F, Kurimoto Y, Kirov I, Shatos M, Coffey P et al. *Multipotent retinal progenitors express developmental markers, differentiate into retinal neurons, and preserve light-mediated behavior. Invest Ophthalmol V is Sci* 2004; 45:4167-73].

To overcome the poor survival and tissue integration associated with subretinal delivery, retinal progenitor cells have been delivered to the retina on solid biomaterial scaffolds [Redenti S, Neeley W L, Rompani S, Saigal S, Yang J, Klassen H et al. *Engineering retinal progenitor cell and scrollable poly(glycerol-sebacate) composites for expansion and subretinal transplantation. Biomaterials* 2009; 30:3405-14; Redenti S, Tao S, Yang J, Gu P, Klassen H, Saigal S et al. *Retinal tissue engineering using mouse retinal progenitor cells and a novel biodegradable, thin-film poly(ecaprolactone) nanowire scaffold. J Ocul Biol Dis Infor* 2008; pp 1-11 In press; Neeley W L, Redenti S, Klassen H, Tao S, Desai T, Young M J et al. *A microfabricated scaffold for retinal progenitor cell grafting. Biomaterials* 2008; 29:418-26; Tad. S, Young C, Redenti S, Zhang Y, Klassen H, Desai T et al. *Survival, Migration and differentiation of retinal progenitor cells transplanted on micro-machined poly(methyl methacrylate) scaffolds to the subretinal space. Lab Chip* 2007; 7:695-701; Tomita M, Lavik E, Klassen H, Zahir T, Langer R, Young M J. *Biodegradable polymer composite grafts promote the survival and differentiation of retinal progenitor cells. Stem Cells* 2005; 23:1579-88]. These tissue engineered porous scaffolds are composed of common synthetic polymers including poly(L-lactic acid)/poly(lactic-co-glycolic acid) (PLLA/PLGA) [Lavik E B, Klassen H, Warfvinge K, Langer R, Young M J. *Fabrication of degradable polymer scaffolds to direct the integration and differentiation of retinal progenitors. Biomaterials* 2005; 26:3187-96], poly(methyl methacrylate) (PMMA) [Tao S, Young C, Redenti S, Zhang Y, Klassen H, Desai T et al. *Survival, migration and differentiation of retinal progenitor cells transplanted on micro-machined poly(methyl methacrylate) scaffolds to the subretinal space. Lab Chip* 2007; 7:695-701], poly(ϵ-caprolactone) (PCL) [Redenti S, Tao S, Yang J, Gu P, Klassen Saigal S et al. *Retinal tissue engineering using mouse retinal progenitor cells and a novel biodegradable, thin-film poly(ecaprolactone) nanowire scaffold. J Ocul Biol Dis Infor* 2008; 1:19-29], or poly(glycerol-sebacate) (PGS) [Redenti S, Neeley W L, Rompani S, Saigal S, Yang J, Klassen H et al. *Engineering retinal progenitor cell and scrollable poly(glycerol-sebacate) composites for expansion and subretinal transplantation. Biomaterials* 2009; 30:3405-14]. They are often coated with laminin to enhance cell adhesion and penetration into the porous polymer scaffold. While important advances have been made, these solid scaffolds do not match the modulus of the retina and lack the flexibility required for subretinal delivery across the damaged retina [Tomita M, Lavik E, Klassen H, Zahir T, Langer R, Young M J. *Biodegradable polymer composite grafts promote the survival and differentiation of retinal progenitor cells. Stem Cells* 2005; 23:1579-88].

Efficient cell delivery and survival are major barriers to successful cellular transplantation. Most transplanted cells die, and those that remain viable either migrate away from the transplant site and/or aggregate together and thus do not integrate with the host tissue [Klassen H J, Ng T F, Kurimoto Y, Kirov I, Shatos M, Coffey P et al. *Multipotent retinal progenitors express developmental markers, differentiate into retinal neurons, and preserve light-mediated behavior. Invest Ophthalmol V is Sci* 2004; 45:4167-73].

SUMMARY

Through the use of innovative biomaterial engineering, cell delivery in an injectable bioresorbable, biocompatible polymer composition comprised of a thermal gelling polymer, an anionic polymer and a water-based solvent can be achieved. Cell delivery in this innovative polymer composition promotes tissue integration without compromising cell survival. This cell delivery polymer composition demonstrates the benefit of an injectable biodegradable polymer as a vehicle for the delivery of cells versus a single-cell suspension in saline. The cellular integration observed is significantly better when cells are delivered in HAMC vs. saline alone. The use of HAMC as a minimally invasive, injectable and bioresorbable strategy for cell delivery to injured or diseased tissue demonstrates the benefit of an appropriately designed biomaterial for greater success of cell therapy. This is true for multiple applications including those in the CNS and retina.

A hydrogel-based system for cellular delivery that allows localized delivery to the subretinal space is provided. A formulation of HAMC meets the design criteria of being minimally invasive, injectable and bioresorbable in situ. The vehicle allows cell survival and proliferation in vitro, and exhibits benefits in overcoming barriers to cell integration in the in vivo studies when compared to saline controls.

The polymer composition comprised of a thermal gelling polymer and an anionic polymer is suitable for cell delivery to either diseased or injured tissue. The injection may be into a cavity that results from disease or injury or the healthy tissue nearby. A polymer composition comprised of hyaluronan (HA) and methylcellulose (MC) is an example of a thermogelling/anionic polymer cell delivery system that promotes cell survival both in vitro and in vivo and is disclosed herein. This composition is referred to as HAMC. Importantly, HAMC (relative to media alone) enhances survival of transplanted stem/progenitor cells in the injured CNS. HAMC provides a minimally invasive cell delivery strategy where the microenvironment can be further defined by incorporation of therapeutically relevant molecules and factors and the differentiation and regenerative capacity further advanced. This hydrogel system has applications for minimally invasive cell delivery to other tissues/organs in the body as well.

Regenerative strategies are limited by poor cellular survival, distribution and integration after transplantation to the injured/diseased tissue. To overcome this limitation a novel cell delivery system is proposed, taking advantage of the minimally invasive, injectable and bioresorbable properties of the polymer composition. For example, HAMC supported CNS derived stem/progenitor cell survival and proliferation in vitro. The polymer composition is a viscous solution, exhibiting properties ideal for delivery in a minimally invasive manner, including delivery to the CNS.

Thus there is disclosed herein, an injectable polymer composition for use as a cell delivery vehicle comprising i) at least one thermal gelling polymer; ii) at least one anionic gelling polymer; and iii) a water-based carrier, wherein the polymer composition is injectable due to its shear thinning properties. This polymer composition may be a gel prior to injection and may return to a gel after injection, depending on the formulation selected.

The thermal gelling polymer may have a molecular weight between 2,000 Da and 1,000,000 Da and the anionic gelling polymer a molecular weight between 100,000 and 7,000,000 Da. The ratio of the thermal gelling polymer to the anionic polymer may be at least from about 0.1:1 to about 20:1 w/w. The ratio of the thermal gelling polymer to the anionic polymer may be 1:1 w/w.

The thermal gelling polymer may be an inverse thermal gelling polymer selected from methylcellulose, a chitosan and beta-glycerophosphate solution, collagen, tri-block copolymer of poly(ethylene glycol)-poly(lactic-co-glycolic acid)-poly(ethylene glycol), tri-block copolymer of poly(propylene glycol)-poly(ethylene glycol)-poly(propylene glycol), diblock copolymer of poly(ethylene glycol)-poly(propylene glycol), poly(N-isopropyl acrylamide), agarose, copolymers of poly-N-isopropylacrylamide, polysaccharides and mixtures thereof.

The anionic gelling polymer may be selected from hyaluronic acid, derivatives of hyaluronic acid, alginate, derivatives of alginate, carboxymethylcellulose, and mixtures thereof. Derivatives of hyaluronic acid have hyaluronic acid as the base polymer with additional chemical groups covalently-bound to the hyaluronic acid (or hyaluronan) such that the physical and/or chemical properties change as a function of the modification. Derivatives of alginate have alginate as the base polymer with additional chemical groups covalently bound to the alginate such that the physical and/or chemical properties change as a function of the modification. Specific chemistries should be familiar to one skilled in the art. However, the following are listed as examples of suitable derivatives: derivatives of hyaluronic acid: ethyl ester derivatives—esterified hydroxyl groups; ethyl esters; benzyl esters; hydrazide derivatives (carbodiimide or other coupling mediated) for protein coupling (RGD sequences for cell adhesion, therapeutic proteins for sustained release) for tyramine substitution—for crosslinking and cell encapsulation sulfate derivatives structurally and chemically similar to heparin (binds non-covalently to proteins such as FGF2, etc.) crosslinked HA (altered rate of degradation); diepoxy crosslinking; biscarbodiimide crosslinking; dihydrazide crosslinking; divinyl sulfone crosslinking; photocrosslinking of methacrylated HA derivative; peptide-derivatives, that is modified with cell-adhesive peptides to promote cell adhesion protein-derivatives; that is HA modified with proteins, growth factors, differentiation factors, etc. to promote specific cellular response such as differentiation.

Derivatives of alginate: carbodiimide protein coupling for cell adhesion (using DCC or DIC couplers, catalyzed by EDC/NHS or EDC/sulfo-NHS—examples can be found in Hermanson, G. *Bioconjugate Techniques. Second edition*, San Diego, Calif.: Academic Press, 1996)—useful for cell delivery: fibronectin binding motif (RGDS); vitronectin binding motif (RGDV); laminin A binding motif (LRGDN); laminin B1 binding motif (YIGSR); collagen 1 binding motif (RGDT); thrombospondin binding motif (RGD); protein coupling for linking bioactive molecules to direct cell survival, proliferation, differentiation, migration; example molecules include VEGF, PDGF, etc.; crosslinked alginate (through carboxylate group using ester, amide, ether, over covalent linkages); amino acid linkers; and amino aldehyde linkers.

Derivatives of MC are also of importance and include MC modified with molecules to promote a specific response by cells, such as cell adhesion, cell differentiation, cell migration, cell guidance, and cell proliferation.

The injectable polymer composition may have a gelling temperature range of from at least 10° C. to at least 70° C.

In one form, the injectable polymer composition comprises methylcellulose (MC) as the thermal gelling polymer and hyaluronic acid (HA) as the anionic gelling polymer. More specifically, the injectable polymer composition may comprise 0.5% w/w methylcellulose and 0.5% w/w hyaluronic acid. The injectable polymer composition may comprise 0.75% w/w methylcellulose and 0.75% w/w hyaluronic acid.

It has been found that the polymer cell delivery vehicle promotes cell survival both in vitro and in vivo relative to a water-based carrier as a cell delivery vehicle.

In addition, the method may involve dispersing the cells or cells and pharmaceutical agent prior to injection to ensure an even distribution of cells and particles, after injection.

Further, the polymer composition used has been found to reduce backflow of cells upon delivery thereby minimizing loss of cells and pharmaceutical agent, the latter when present.

The injectable polymer composition may be injected by one of the following methods: transdermal, oral, sub-mucosal, sub-cutaneous, intranasal, vaginal, buccal, intrathecal, epidural, intraparenchymal to the brain or spinal cord, ocular, subretinal spaces, dental, intratumoral, intramuscular, cardiac, intraarticular, intravenous, cavities created surgically for therapeutic intervention, cavities resulting from disease, and cavities resulting from injury.

The injectable polymer composition may include at least one cell type selected from mammalian cells, stem, precursor and progenitor cell populations isolated from the adult or embryonic: brain, neural subventricular zone, hippocampal subgranular zone, spinal cord, skin, blood, mesenchyme, umbilical cord, skin-derived precursors or adult retinal ciliary epithelium and their undifferentiated and differentiated progeny; embryonic stem cells and their undifferentiated and differentiated progeny; epiblast stem cells and their undifferentiated and differentiated progeny; primitive and definitive neural stem cells and their undifferentiated and differentiated progeny; induced pluripotent stem cells and their undifferentiated and differentiated progeny; mesenchymal stem cells and their undifferentiated and differentiated progeny; bone-marrow derived stem cells and their undifferentiated and differentiated progeny; hematopoietic stem cells and their undifferentiated and differentiated progeny; umbilical cord derived stem/progenitor cells and their undifferentiated and differentiated progeny; neural precursor cells of the forebrain, midbrain, hindbrain, spinal cord, neural crest, and retinal precursors isolated from developing tissue and their undifferentiated and differentiated progeny.

The cells may be delivered as spheres, aggregates or single cell suspensions.

The injectable polymer composition may also include at least one pharmaceutical agent.

The pharmaceutical agent may be selected from the group comprising: anesthetics for use in caudal, epidural, inhalation, injectable, retrobulbar, and spinal applications; analgesics, selected from the group comprising acetaminophen, ibuprofen, fluriprofen, ketoprofen, voltaren, phenacetin and salicylamide; anti-inflammatories selected from the group comprising naproxen and indomethacin; antihistamines, selected from the group comprising chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussives selected from the group comprising dextromethorphan hydrobromide and guaifenesin; expectorants; decongestants, selected from the group comprising phenylephrine hydrochloride, phenylpropanolamine hydrochloride, pseudoephedrine hydrochloride, and ephedrine; antibiotics selected from the group comprising amebicides, broad and medium spectrum, fungal medications, monobactams and viral agents; bronchodilators selected from the group comprising theophylline, albuterol and terbutaline; cardiovascular preparations selected from the group comprising diltiazem, propranolol, nifedepine, clonidine, alpha adrenoceptor agonists, alpha receptor blocking agents, alpha and beta receptor blocking agents, antiotensin converting enzyme inhibitors, beta blocking agents, calcium channel blockers, and cardiac glycosides; central nervous system drugs selected from the group comprising thioridazine, diazepam, meclizine, ergoloid mesylates, chlorpromazine, carbi- dopa and levodopa; metal salts selected from the group comprising potassium chloride and lithium carbonate; minerals selected from the group consisting of iron, chromium, molybdenum and potassium; immunomodulators; immunosuppressives selected from the group comprising minocycline, cyclosporine A; thyroid preparations selected from the group comprising synthetic thyroid hormone, and thyroxine sodium; peptide and glycoprotein hormones and analogues selected from the group comprising human chorionic gonadotrophin (HCG), corticotrophin, human growth hormone (HGH—Somatotrophin) and erythropoietin (EPO); steroids and hormones selected from the group comprising ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, and GM1 ganglioside; small molecules, including taurine, retinoic acid, sodium butyrate, cAMP, dbcAMP; small molecule hydrophobic drugs; vitamins selected from the group comprising water-soluble vitamins and veterinary formulations; growth factors, proliferative factors and morphogens including, but not limited to, EGF, FGF2, FGF1, EPO, PDGF-AA, PDGF-BB, BDNF, GDNF, CNTF, VEGF, SHH, IFN-γ, and neurotrophins; peptides, peptide mimetics and other protein preparations; anti-angiogenics selected from the group comprising, but not limited to, ranibizumab, bevacizumab, and pegaptanib; DNA; and, small interfering RNAs; and when required a pharmaceutically acceptable carrier or preservative.

The pharmaceutical agent may be encapsulated in micron-sized particles or nanoparticles selected from microspheres, micron-sized rods, nanospheres, nanorods and liposomes.

There may be present in the injectable polymer composition a non-covalent interaction between the particles/rods/liposomes described above and the polymers of the thermal and anionic gel to promote the distribution of the particles throughout the gel. This non-covalent interaction may involve ionic (such as between canonically-charged particles and anionically-charged polymer), hydrophobic, hydrogen bonding, electrostatic, among others. For example, a cationic/anionic combination may promote distribution of the microspheres, nanoparticles or liposomes from the matrix. A charge stabilizer may be added to promote an interaction between the polymer composition and the pharmaceutical. Further, the pharmaceutical may be covalently bonded to at least one of the thermal gelling polymer and the anionic gelling polymer. The pharmaceutical agent may also be incorporated or encapsulated into the micro- or nano-particle/rod to provide a method for its sustained release.

The injectable polymer may be used for delivery of the pharmaceutical agents described above including neuroprotective, angiogenic, anti-angiogenic or neuroregenerative pharmaceuticals, or for delivery of at least one factor capable of stimulating endogenous stem cells. The polymer composition may be bioresorbable and the composition may be formulated for sustained release over a broad time range, from hours to days to months to years.

To overcome the barriers of cell survival and integration after subretinal transplantation, there is disclosed a minimally invasive, injectable, and biodegradable vehicle for cellular delivery. Minimally invasive ophthalmological procedures are associated with lower patient morbidity [Kubitz J C, Motsch J. *Eye surgery in the elderly. Best Pract Res Clin Anaesthesiol* 2003; 17:245-57]. Using a minimally invasive technique, the injection site may be self-healing without the need for sutures. Using a physical matrix, cells can be preloaded promoting even distribution after transplantation in the subretinal space. Importantly, by using a bioresorbable biomaterial, permanent retinal detachment due to material placement is not a concern at the transplantation site. This allows the tissue layers to heal together, and prevents pathologic fibrosis that disrupts normal retinal function.

The micron-sized particles that incorporate the pharmaceutical agents are dispersed in the polymer along with the cells prior to injection to ensure an even distribution of cells and microspheres.

This disclosure encompasses the use of the injectable polymer composition for delivery of neuroprotective, angiogenic, anti-angiogenic or neuroregenerative pharmaceuticals. Delivery of at least one factor capable of stimulating endogenous stem cells is also contemplated.

The method includes cell delivery to a site requiring repair, treatment or regeneration. The treatments may include cosmetic and therapeutic uses. Most particularly the cell delivery is to a central nervous system site for any one of repair, regeneration or treatment. In such instance, the cells may be central nervous system derived stem-progenitor cells.

Where the cell type is a mammalian cell, it is added to the polymer composition by the steps of:

a) centrifuging the mammalian cells which are selected from cultured in vitro spheres, aggregates and single cells to obtain a pellet;

b) suspending the cells in a biocompatible solution such as media or buffer; and c) mixing the cell suspension with the injectable polymer composition.

The injectable polymer composition may be used to deliver a therapeutically effective amount of mammalian between 10,000 cells to about 200 million cells. Usually the cells and micron-sized particles that encapsulate the pharmaceutical agents are dispersed in the injectable polymer composition to ensure an even distribution of cells and microspheres.

It is envisaged that the composition may be administered to a patient for treatment of a disease selected from the group consisting of cancer, stroke, genetic disorders, liver disorders, development disorders, degenerative disorders, familial or traumatic disorders of the nervous system, vascular disorders, skin diseases, skin disorders, auto immune disorders, eye disorders, kidney disorders, cardiac disorders, muscoskeletal disorders, reproductive disorders, fertility disorders, and blood disorders, with the appropriate cell types and pharmaceuticals being included. Treatments of particular interest are those for repair of spinal cord injury, stroke and retinal degenerative disease.

DETAILED DESCRIPTION

Figure 1:
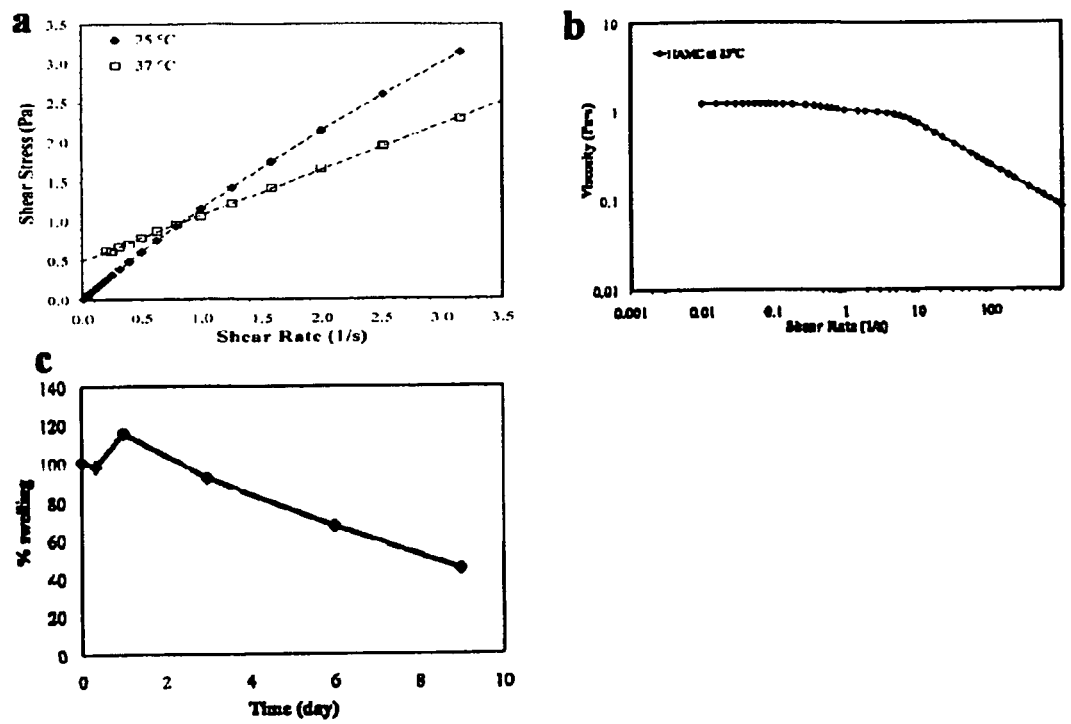
FIG. 1 illustrates how HAMC was characterized by: (a) shear stress vs. shear rate, demonstrating a yield stress at 37° C.; (b) viscosity vs. shear rate, demonstrating shear-thinning; and (c) swelling.

The injectable hydrogel cell delivery vehicle has been found to be very useful in the central nervous system, namely in the brain, spinal cord and retina. Experiments have been conducted after spinal cord injury, neural stem/progenitor cells (derived from the brain or spinal cord) injected within HAMC into the cavity that forms after traumatic injury in animal models. The HAMC/stem cells can be injected in acute, sub-acute or chronic injured animals. HAMC/stem cells were injected either at 7, 9 or 14 days after the initial injury. Cell viability was 100% greater when cells were delivered in HAMC vs. saline controls to the injured CNS tissue. Similar studies have been conducted in the brain, where HAMC served as a cell delivery vehicle to the cavity that formed after stroke injury. Four days after stroke injury, cells were injected in HAMC to the lesion site/cavity that had formed. Based on this work, it would seem that similar results could be obtained using different cell types, as appropriate in other areas of the body.

The injectable polymer hydrogel can be used to co-deliver cells and pharmaceutical agents encapsulated in a micron-sized particle or nanoparticle selected from microspheres, micron-sized rods, nanospheres, nanorods and liposomes. The cells and micron-sized particles, for example poly(lactic-co-glycolic acid) (PLGA) microspheres, can be dispersed in HAMC prior to injection to ensure an even distribution of cells and microspheres. Additionally, growth factors, proteins, peptides and small molecules selected for enhancing survival and promoting differentiation in vitro can be encapsulated into these microspheres for controlling the in vivo survival and/or differentiation of transplanted cells.

The selection of pharmaceutical agents to be encapsulated into these drug delivery vehicles, maybe based on in vitro screens designed to identify target molecules that enhance survival or differentiation of stem/precursor cells. For example, an in vitro screen has shown that dibutyryl cyclic AMP (dbcAMP) and interferon-gamma (IFN-γ), alone or in combination, enhanced neuronal differentiation most significantly compared to a number of candidate molecules that had been previously implicated in neuronal differentiation including brain-derived neurotrophic factor (BDNF), dbcAMP, IFN-γ, nerve growth factor (NGF), neurotrophin-3 (NT3), sonic hedgehog (Shh), retinoic acid (RA), and 1% fetal bovine serum (FBS) as a control.

Cell delivery to the retina has also been examined. Specifically, to the sub-retinal space, a series of natural polymer hydrogels were first screened for physical properties of flow and gelation time, and biological properties of retinal stem-progenitor cell (RSPC) growth and cell survival. Agarose [Tschon M, Fini M, Giavaresi G, Torricelli P, Rimondini L, Ambrosio L et al. *In vitro and in vivo behaviour of biodegradable and injectable PLA/PGA copolymers related to different matrices. Int J Artif Organs* 2007; 30:352-62], collagen [Wallace D G, Rosenblatt J. *Collagen gel systems for sustained delivery and tissue engineering. Advanced Drug Delivery Reviews* 2003; 55:1631-49], chitosan/glycerol-phosphate [Chemte A, Chaput C, Wang D, Combes C, Buschmann M D, Hoemann C D et al. *Novel injectable neutral solutions of chitosan form biodegradable gels in situ. Biomaterials* 2000; 21:2155-61], and HAMC (a physical blend of hyaluronan and methylcellulose) were included in the screen because all of these materials had literature precedence for injectability and simple gelation mechanisms. HAMC has been previously shown to exhibit rapid thermally-reversible gelation in situ, biocompatibility, bioresorbability and a useful intrathecal drug delivery vehicle in the central nervous system (CNS) [Gupta D, Tator C H, Shoichet M S. *Fast-gelling injectable blend of hyaluronan and methylcellulose for intrathecal, localized delivery to the injured spinal cord. Biomaterials* 2006; 27:2370-9; Kang C E, Poon P C, Tator C H, Shoichet M S. *A new paradigm for local and sustained release of therapeutic molecules to the injured spinal cord for neuroprotection and tissue repair. Tissue Eng Part A* 2009; 15:595-604; Baumann M D, Kang C E, Stanwick J C, Wang Y, Kim H, Lapitsky Y et al. *An injectable drug delivery platform for sustained combination therapy. J Control Release* 2009; 138: 205-13]. Based on these series of in vitro screens, HAMC was then pursued for in vivo studies where it was further evaluated for degradation and cell delivery. The HAMC formulation is particularly compelling because MC forms physical, hydrophobic interactions while HA is known to promote wound healing following CNS injection [Gupta D, Tator C H, Shoichet M S. *Fast-gelling injectable blend of hyaluronan and methylcellulose for intrathecal, localized delivery to the injured spinal cord. Biomaterials* 2006; 27:2370-9; Shoichet M S, Tator C H, Poon P, Kang C, Douglas Baumann M *Intrathecal drug delivery strategy is safe and efficacious for localized delivery to the spinal cord. Prog Brain Res* 2007; 161:385-92; Balazs E A. *Medical applications of hyaluronan and its derivatives. J Polym Mater Sci Eng* 1990; 63:689-91; Balazs E A, Bland P A, Denlinger J L, Goldman A L Larsen N E, Leshchiner E A et al. *Matrix engineering. Blood Coagul Fibrinolysis* 1991; 2:173-8] and is non-immunogenic and biocompatible [Vercruysse K P, Prestwich G D, Kuo J W *Hyaluronate derivatives in drug delivery. Crit. Rev Ther Drug Carrier Syst* 1998; 15:513-55]. Moreover, HA is a prominent constituent of the interphotoreceptor matrix in humans, where it functions as a basic scaffold to which other macromolecules attach [Hollyfield J G. *Hyaluronan and the functional organization of the interphotoreceptor matrix. Invest Ophthalmol V is Sci* 1999; 40:2767-9; MacLaren, R. E., Pearson, R. A., MacNeil, A., Douglas, R. H., Salt, 7'. E., Akimoto, M., Swaroop, A., Sowden, J. C., and Ali, R. R. *Retinal repair by transplantation of photoreceptor precursors. Nature* 2006; 44:203-207]. A formulation and role for HAMC as a cell delivery vehicle was developed by investigating cellular compatibility, in vivo biodegradability or bioresorbability, and characteristics of integration of retinal stem-progenitor cells (RSPCs) in the subretinal space.

In vivo transplantation studies in mice were carried out to investigate both the biodegradability of HAMC in the sub-retinal space over 7 days and the potential of HAMC as a cell delivery vehicle. RSPCs delivered in HAMC were more evenly distributed in the subretinal space than those delivered in traditional saline solutions, suggesting that HAMC is a promising vehicle for cellular delivery to the degenerating CNS including the spinal cord, brain and retina overcoming previously reported barriers to tissue integration such as cellular aggregation and non-contiguous distribution.

Choosing the appropriate hydrogel for cell delivery is challenging as the hydrogel must be injectable via a minimally-invasive strategy to avoid further tissue damage, to be bioresorbable and biocompatible and to support cell survival. It has been previously demonstrated that a blend of 2 wt % hyaluronan (HA) and 7 wt % low-molecular-weight methyl cellulose (MC) designed for drug delivery, meets a number of these design criteria and in fact, has some therapeutic benefit in terms of improved function and reduced inflammatory response relative to controls in a spinal cord injury model [Neeley W L, Redenti S, Klassen H, Tao S, Desai T, Young M J et al. *A microfabricated scaffold for retinal progenitor cell grafting. Biomaterials* 2008; 29:418-26]. HA is a glycosaminoglycan that plays a major structural role in the formation of brain extracellular matrix (ECM) [Shoichet M S, Tator C H, Poon P, Kang C, Douglas Baumann M *Intrathecal drug delivery strategy is safe and efficacious for localized delivery to the spinal cord. Prog Brain Res* 2007; 161:385-92; Balazs E A. *Medical applications of hyaluronan and its derivatives. J Polym Mater Sci Eng* 1990; 63:689-91]. It has been used extensively in vivo because of its non-immunogenic and biocompatible properties [Balazs E A, Bland P A, Denlinger J L, Goldman A I, Larsen N E, Leshchiner E A et al. *Matrix engineering. Blood Coagul Fibrinolysis* 1991; 2:173-8]. Moreover, it promotes wound healing by reducing inflammation and minimizing tissue adhesion and scar formation, [Vercruysse K P, Prestwich G D, Kuo J W. *Hyaluronate derivatives in drug delivery. Crit. Rev Ther Drug Carrier Syst* 1998; 15:513-55], and promotes the regeneration of the punctured dura after its injection into the intrathecal space [Neeley W L, Redenti S, Klassen H, Tao S, Desai T, Young M J et al. *A microfabricated scaffold for retinal progenitor cell grafting. Biomaterials* 2008; 29:418-26]. Methylcellulose, the other major constituent of HAMC, has inverse thermal gelling properties, and at physiological ionic strength undergoes thermoreversible gelation when heated. The gelation temperature depends on the salt concentration or the presence of anionic groups, including those of hyaluronic acid. The composition designed for drug delivery (2% HA, 7% MC) was not suitable for cell delivery because of its high viscosity and dense network formation. Hence, a specific in situ thermogelling cell delivery system specifically formulated for localized cell delivery is proposed. The formulation, consists of 0.5 wt % HA and 0.5 wt % MC and provides a permissive environment for culturing cells while preserving the thermogelling properties of the original formulation. The thermogelling characteristic of the HAMC cell delivery system is important for ensuring that the transplanted cells remain distributed within the three-dimensional polymeric gel that fills the cavity.

Importantly, HAMC impacts neither cell survival nor normal cellular growth. Cell survival and proliferation were assessed separately, a distinction that has been neglected in previous biomaterial-cell delivery studies [Redenti S, Neeley W L, Rompani S, Saigal S, Yang J, Klassen H et al. *Engineering retinal progenitor cell and scrollable poly(glycerol-sebacate) composites for expansion and subretinal transplantation. Biomaterials* 2009; 30:3405-14; Hermanson, G. *Bioconjugate Techniques. Second edition*, San Diego, Calif.: Academic Press, 1996]. It has been demonstrated that sphere growth is a good proxy for proliferation and not sphere aggregation. These results are consistent with those of Mori et al., who showed that coalescence in neural stem cell culture is observed only from the merging of small cell aggregates in immature cultures but not by mature neurospheres [Ballios, B. G., Clarke, L., Coles, B. L. K, Cooke, M. J., Shoichet, M. S., van der Kooy, D. *A bioengineered delivery strategy improves the transplantation of retinal stem cells and differentiated progeny. Program No.* 737.16. 2010 *Neuroscience Meeting Planner.* Washington, D.C.: Society for Neuroscience, 2010. San Diego, Calif., Nov. 13-17, 2010]. More consistent cell viability over culture time of the spheres vs. single cells, has been demonstrated suggesting a benefit for the delivery of spheres. Moreover, the autocrine/paracrine signaling between cells, such as endogenous secretion of FGF2 by closely associated cells, as is normally observed in RSPC sphere colonies [Tropepe V, Coles B L K, Chiasson B J, Horsford D J, Elia A J, McInnes R R et al. *Retinal stem cells in the adult mammalian eye. Science* 2000; 287:2032-36; Coles B L K, Angenieux B, Inoue T, Rio-Tsonis K, Spence J R, McInnes R R et al. *Facile isolation and the characterization of human retinal stem cells. Proc Natl Acad Sci USA* 2004; 101:15772-7]. The injection of single cells is also beneficial because single cells may be more easily injected through the fine 34-gauge needle in the subretinal transplant and ultimately single cells are likely to integrate with the host tissue better.

Importantly, HAMC maintains a distribution of cells during the in vitro cell culture, as demonstrated by confocal reconstruction. Thus, HAMC overcomes the problems of cellular aggregation and provides greater opportunity for cellular integration with host tissue. Cells dispersed in HAMC did not aggregate over the 6 day culture period, providing further evidence that mixing cells in HAMC inhibits cellular aggregation prior to transplantation. These cell distribution phenomena are not often studied in the context of cellular delivery using injectable biomaterials, but are essential to anticipating and understanding the behavior of the system in vivo.

The in vivo experiments confirm the use of HAMC as a minimally invasive, injectable and biodegradable cell delivery vehicle. The ability to inject a fluidic vehicle without the inherent risk of retinal microstructure damage that might arise during the placement of a solid, cell-seeded scaffold confers an important practical benefit. The use of this cell delivery vehicle is a step towards the development of safe biomaterials for the treatment of retinal diseases. The positive attributes observed with HAMC for cell delivery to the retina can be generalized to other tissues of the CNS and other tissues in general. HAMC is viscous on injection, with no observed backflow on needle retraction or clogging of the 34 G needle. Its non-cell adhesive properties [Gupta D, Tator C H, Shoichet M S. *Fast-gelling injectable blend of hyaluronan and methylcellulose for intrathecal, localized delivery to the injured spinal cord. Biomaterials* 2006; 27:2370-9] minimize scar formation and its biologically neutral impact on cell survival and growth allows transplanted cells to respond to endogenous cues that may promote integration.

Dissection and fluorescent labeling combined with confocal reconstruction indicated that HAMC filled the subretinal space evenly and degraded over a one week period. No changes in retinal morphology were observed. The in vivo degradation profile of both HA and MC in the subretinal space was slower than that observed in the intrathecal space [Kang C E, Poon P C, Tator C H, Shoichet M S. *A new paradigm for local and sustained release of therapeutic molecules to the injured spinal cord for neuroprotection and tissue repair. Tissue Eng Part A* 2009; 15:595-604], where similar materials have been used previously, likely because of continuous CSF flow in the intrathecal space which is absent in the subretinal space. However, similar to the intrathecal studies, HA was observed to degrade more rapidly than MC. Endogenous hyaluronidase is present in the normal eye [Kunishima, M; Kawachi, C.; Morita, J.; Terao, K; Iwasaki, F.; Tani, S. 4-(4,6-*dimethoxy*-1,3,5-*triazin*-2-*yl*)-4-*methyl-morpholinium chloride: an efficient condensing agent leading to the formation of amides and esters. Tetrahedron* 1999; 55; 13159-13170] and pathologic retina [Ellman, G. D. *Tissue sulfhydryl groups. Archives of Biochemistry and Biophysics* 1959; 82; 70-72], and can serve to degrade the HA. In support of these known mechanisms of HA degradation, this component showed a punctate appearance within the first few hours following injection. This corresponds to bulk degradation throughout the entire material, contrasted with surface degradation which would show preferential erosion of HA fluorescence at the periphery. This is consistent with previous work, which shows that HAMC presents minimal resistance to molecular diffusion of molecules up to 150 kDa [Baumann M D, Kang C E, Stanwick J C, Wang Y, Kim H, Lapitsky Y et al. *An injectable drug delivery platform for sustained combination therapy. J Control Release* 2009; 138:205-13]. Therefore, hyaluronidase (53.9 kDa) may diffuse freely throughout the gel.

Compared to saline delivery of RSPCs, HAMC delivery decreased cellular aggregation and promoted cellular distribution in the subretinal space. Following transplantation, the majority of cells integrate in the RPE layer, adopting a cuboidal morphology. This cell delivery strategy may be useful for the treatment of widespread or advanced maculopathy, where large areas of the RPE are destroyed [Ballios, B. G., Clarke, L., Coles, B. L. K, Cooke, M. J., Shoichet, M. S., van der Kooy, D. *A bioengineered delivery strategy improves the transplantation of retinal stem cells and differentiated progeny. Program No.* 737.16. 2010 *Neuroscience Meeting Planner. Washington, D.C.: Society for Neuroscience,* 2010. San Diego, Calif., Nov. 13-17, 2010]. The choroidal neovascularization inherent in wet-AMD is marked by widespread disruption of the RPE and disturbance of the homeostatic mechanisms of photoreceptor outer segment phagocytosis [Arden G B, Sidman R L, Arap W, Schlingemann R O. *Spare the rod and spoil the eye. Br J Ophthalmol* 2005; 89:764-9; Elizabeth Rakoczy P, Yu M J™ Nusinowitz S, Chang B, Heckenlively J R. *Mouse Models of age-related macular degeneration. Exp Eye Res* 2006; 82:741-52; and Ding X, Patel M, Chan C C. *Molecular pathology of age-related macular degeneration. Prog Retin Eye Res* 2009; 28:1-18] The RPE replacement potential demonstrated by the HAMC delivery system is therefore therapeutically relevant to the treatment of AMD.

Efficient cell delivery and survival are major barriers to successful cellular transplantation in the CNS. Most transplanted cells die, and those that remain viable either migrate away from the transplant site and/or aggregate together and thus do not integrate with the host tissue [Klassen H J, Ng T F, Kurimoto Y, Kirov I, Shatos M, Coffey P et al. *Multipotent retinal progenitors express developmental markers, differentiate into retinal neurons, and preserve light-mediated behavior. Invest Ophthalmol V is Sci* 2004; 45:4167-73]. The data presented here show that, through the use of innovative biomaterial engineering, cell delivery in HAMC promotes tissue integration without compromising cell survival. While there are a few other reports of biodegradable polymeric scaffolds studied for cell transplantation in the retina [Redenti S, Neeley W L, Rompani S, Saigal S, Yang J, Klassen H et al. *Engineering retinal progenitor cell and scrollable poly(glycerol-sebacate) composites for expansion and subretinal transplantation. Biomaterials* 2009; 30:3405-14; Redenti S, Tao S, Yang J, Gu P, Klassen H, Saigal S et al. *Retinal tissue engineering using mouse retinal progenitor cells and a novel biodegradable, thin-film poly(ecaprolactone) nanowire scaffold. J Ocul Biol Dis Infor* 2008; 1:19-29; Neeley W L, Redenti S, Klassen H, Tao S, Desai T, Young M J et al. *A microfabricated scaffold for retinal progenitor cell grafting. Biomaterials* 2008; 29:418-26; Tao S, Young C, Redenti S, Zhang Y, Klassen H, Desai T et al. *Survival, migration and differentiation of retinal progenitor cells transplanted on micro-machined poly(methyl methacrylate) scaffolds to the subretinal space. Lab Chip* 2007; 7:695-701; and Tomita M, Lavik E, Klassen H, Zahir T, Langer R, Young M J. *Biodegradable polymer composite grafts promote the survival and differentiation of retinal progenitor cells. Stem Cells* 2005; 23:1579-88], this is the first report to test and demonstrate the benefit of an injectable biodegradable polymer as a vehicle for the delivery of cells versus a single-cell suspension in saline. The cellular integration observed is significantly better when cells are delivered in HAMC vs. saline alone. The use of HAMC as a minimally invasive, injectable and biodegradable strategy for cell delivery to the damaged retina demonstrates the benefit of an appropriately designed biomaterial for greater success of cell therapy in the CNS.

A hydrogel-based system for cellular delivery that allows localized delivery to the subretinal space was developed and characterized. A formulation of HAMC meets the design criteria of being minimally invasive, injectable and bioresorbable in situ. The vehicle allows cell survival and proliferation in vitro, and exhibits benefits in overcoming barriers to cell integration in the in vivo studies when compared to saline controls.

EXAMPLES

The following examples describe several aspects of embodiments in greater detail. These examples are provided to further illustrate, not to limit, aspects of the disclosure and claims set forth herein.

Example 1

In Vitro Characterization of HAMC as a Cell Delivery Vehicle

1. Composition of 0.5% Hyaluronic Acid and 0.5% Methylcellulose

The thermogelling HAMC composition was prepared using HA (MW 1,500,000, Novamatrix, Norway) and MC (MW 310,000, ShinEtsu Metolose SM-4000, Japan) and media. Both polymers were sterile-filtered as dilute solutions through 0.2 μm mesh filters (Nalgene, Rochester, N.Y., USA) and lyophilized prior to use. To form the composition, 0.5 wt % HA and 0.5 wt % MC were dissolved in media at room temperature and refrigerated until used. HAMC rheology was characterized via stress-controlled steady state experiments at 25° C. and 37° C., using a TA Instruments AR2000 rheometer equipped with a 60-mm 0.5° cone. To allow thermal equilibration to occur, all samples were conditioned for 20 minutes prior to shear. Measurements were then performed at shear stresses ranging between 0.01 and 80 Pa at both 25 and 37° C.

2. Measurement of Gelation Rates of HAMC

300 μl HAMC made in basic medium was injected into the bottom of a 1.7 ml microcentrifuge tube (Fisher Scientific, Ottawa, ON, CA) and incubated at 37° C. At 5, 10, 12, 14, 16, 18, 20 min. intervals, tubes were inverted to observe if the gel flowed. The time at which the gel did not flow was recorded as the gelation time.

The 0.5/0.5 w/w % HAMC hydrogel was characterized by time to gelation, viscosity, rheology and swelling (FIG. 1a-c). By the inverted tube test, HAMC gels after 18 min at 37° C.

3. Evaluation of the Thixotropic Properties of HAMC

At room temperature HAMC is a moderately viscous solution with shear thinning properties as shown in FIG. 1A. This Theological signature is characteristic for polymeric compositions [Hermanson, G. *Bioconjugate Techniques. Second edition*, San Diego, Calif.: Academic Press, 1996], where the viscosity, $\eta$ stays nearly constant ($\eta=1.2$ Pa·s) at low shear rates and decreases with a power law relationship at high shear rates (in this case, with a scaling exponent of ~0.5). The shear stress ($\tau$) vs. shear rate ($\dot{\gamma}$) data in the limit of low shear rate for HAMC at both 25 and 37° C. are illustrated in FIG. 1B. At 25° C., the rheological response in this limit is nearly-Newtonian (i.e., linear shear stress vs. shear rate relationship without a yield stress, where ($\tau=\eta\cdot\dot{\gamma}$), reflecting the nearly constant viscosity in the low-shear portion of the flow curve. Heating to 37° C., however, gives rise to a yield stress, which is the stress required to break the network and force the composition to flow and is given by the y-intercept in the shear stress vs. shear rate curve. Thus, the composition exhibits nearly perfect Bingham plastic behavior, according to $\tau=\mu_p\cdot\dot{\gamma}+\tau_y$, where $\mu_p$ is the plastic viscosity, and $\tau_y$ is the yield stress. Fitting the experimental data to this model yields a plastic viscosity of approximately 0.6 Pa·s and a yield stress of 0.5 Pa, which corresponds to the formation of a very weak gel. Importantly, this data showed that the material could be injected without putting lethal stress on NSPCs and would gel upon injection.

4. Evaluation of Polymer Matrix Swelling

100 μl of 0.5/0.5 w/w % HAMC made in media was added to a 1.7 ml eppendorf tube that was equilibrated at 37° C. On the top of the gel, 900 μl of 37° C. artificial cerebrospinal fluid (aCSF): 0.5 mM NaCl, 5 mM KCl, 1.3 mM MgCl$_2$, 0.1 mM CaCl$_2$, 26 mM NaHCO$_3$, and 10 mM D-glucose, pH 7.4, was added. After set-up, half of the media was removed from the tubes every 24 h and exchanged with fresh incubation media. To study the trend transiently, samples were collected at each time point. At 0, 8 h, 1, 3, 6, 9 days of incubation, all the media was removed and the weight of the wet gel was recorded (n=4). The polymer samples were snap frozen and dried using the freeze dryer, and the remaining polymer mass was weighed. Swelling was quantified as a function of time.

$$\% \text{ swelling} = \frac{\text{wet gel weight}(t)}{\text{wet gel weight}(t=0)} \times 100\%$$

Since HAMC is designed to be injected into a tissue cavity, the degree of gel swelling was investigated to ensure minimal tissue damage such as compression of the soft tissue at the injured site. The swelling of HAMC reached a maximum swollen volume of approximately 115% by 1 day and gradually decreased to 50% by day 9 (FIG. 1C).

5. Evaluation of Polymer Impact on Survival and Proliferation of CNS Derived Stem/Progenitor Cells In Vitro Retinal Stem Cells Cell survival and proliferation in HAMC was studied. Following 7 days of primary culture of actin-GFP retinal stem/progenitor cells, spheres were either mixed directly with hydrogels reconstituted in growth media, or dissociated into a single cell suspension in a manner identical to pre-transplantation cell preparation. Survival was assayed using fluorescence imaging and single cell counting, with ethidium homodimer-1 (EthD-1, 10 μM final concentration) (Invitrogen, Burlington, ON) used to mark dead cells. Proliferation was assayed by measuring the sphere diameter over 6 days of culture in the polymer matrix. Staining and fluorescence was visualized using a ZeissAxio Observer.D1 inverted fluorescent microscope equipped with an AxioCamMRm digital camera, and imaged using ZeissAxioVision V4.6 software. Significance is noted only if p<0.05, as determined by using standard Student's t-test.

Figure 2A:
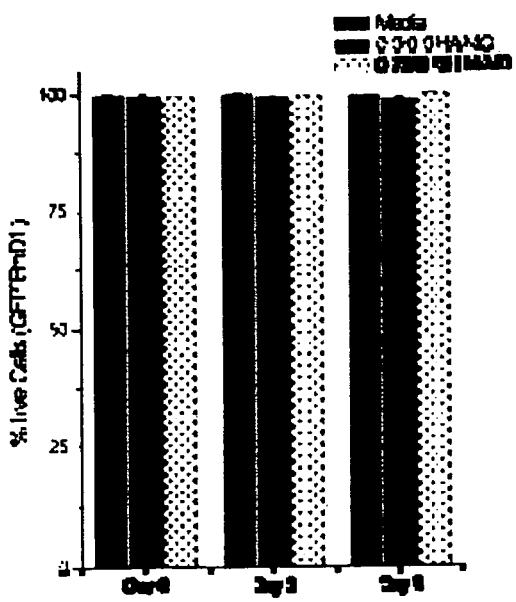
FIG. 2 illustrates in vitro characterization of RSPC loaded HAMC. Viability data for cells distributed in 0.5/0.5% HAMC as (a) whole spheres and (b) dissociated sphere single-cell suspension. Representative micrographs of (c) a whole sphere and (d) dissociated sphere suspensions in HAMC over 6 day culture (scale 100 μm). Note, some dissociated cells are out of the plane of focus.
Figure 2B:
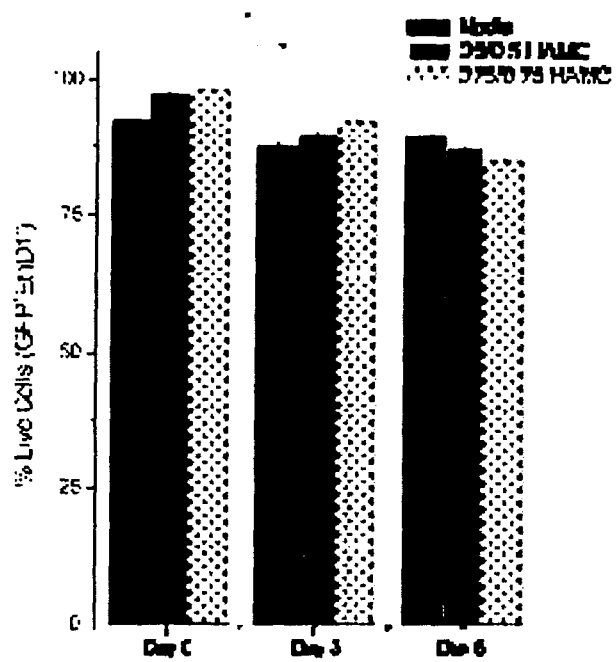
Figure 2C:
Figure 2D:

Live cells, identified as GFP-positive and EthD-negative, were constant across all culture conditions (media, HAMC 0.5/0.5 and HAMC 0.75/0.75) for spheres (FIG. 2A) and single cells (FIG. 2B). While there was no significant difference across the groups at each time point, there was a decrease in cell viability after 3 days of culture of single cells (in all conditions) relative to both time of plating (t=0) and spheres. RSPC sphere diameter, reflective of proliferative cell division, was not significantly different between control media and the HAMC 0.5/0.5 composition over 6 days: day 0: media 84±2 μm vs. HAMC 71±11 μm; day 3: media 103±7 μm vs. HAMC 83±15 μm; day 6: media 130±17 μm vs. HAMC 142±4 μm.

Forebrain-Derived Neural Stein Cells

Neural stem/progenitor cells (NSPCs) were collected from cell culture wells into a 1.7 ml eppendorf tube, spun down at 3000 rpm for 5 min and washed once in sterile PBS. NSPCs were lysed through a freeze-thaw cycle in 1× Tris-EDTA buffer and 0.2% Triton X-100™ (Sigma-Aldrich). Total double stranded DNA was measured by fluorescence (Molecular Devices) by the reaction of DNA with PicoGreen (PicoGreen dsDNA Quantitation Kit; Invitrogen). An internal standard curve was prepared and used to convert the concentration of dsDNA to total number of cells. The data were expressed as fold growth relative to number of NSPCs seeded at time zero.

Figure 3:
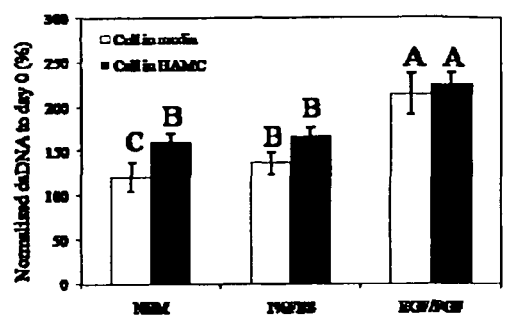
FIG. 3 illustrates NSPC neurospheres cultured in proliferation media alone vs. proliferation media in HAMC after 4 days. The PicoGreen assay for dsDNA shows a greater number of cells in the EGF/FGF2 proliferation media and comparable numbers for cells cultured in media or HAMC.

The number of NSPCs cultured in HAMC was compared to those in media after 4 days of culture using the dsDNA content by the Picogreen assay as a proxy for cell number. Importantly, cells cultured in HAMC were injected via a 30-gauge needle into the culture well, thereby simulating the in vivo injection procedure. The day 4 data was normalized to day 0 to account for any variability in the number of NSPCs seeded. The number of NSPCs cultured in media was comparable to those dispersed in HAMC (FIG. 3). In basic culture conditions, there were more live cells in HAMC relative to the media control. While no significant difference was observed among cells grown in media vs. HAMC for the other media conditions, NSPCs grew more rapidly when cultured in the presence of mitogens (EGF/FGF2) than the basal and differentiation media conditions.

6. Evaluation of Distribution of Cells in 3D Polymer Matrix Retinal Stem Cells

Figure 4:
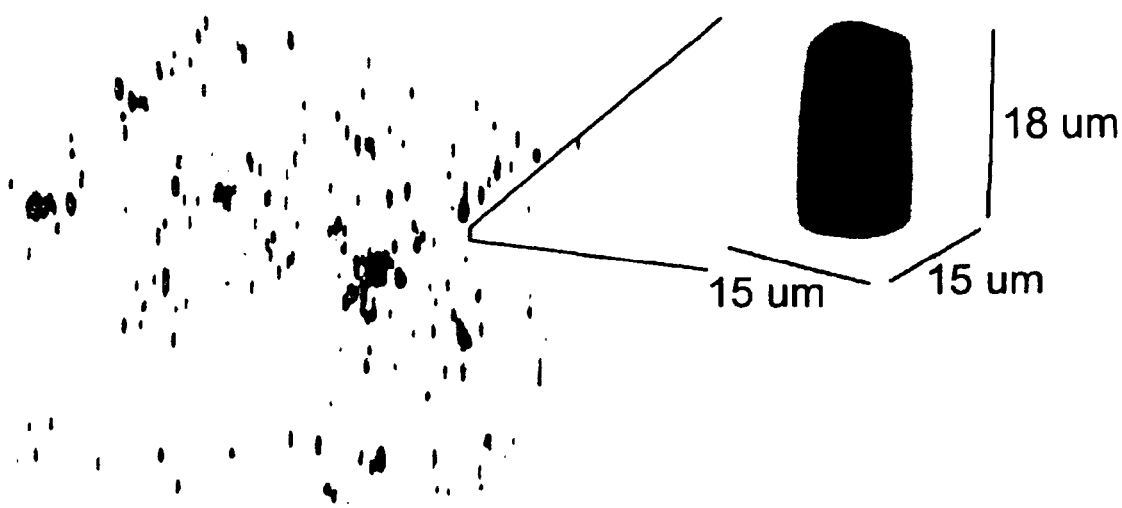
FIG. 4 illustrates confocal reconstruction of dissociated GFP+RSPC suspension in 0.5/0.5% HAMC illustrating random cellular distribution and inhibition of cellular aggregation and settling (volume: 1.7 mm$^3$). Single cell included for scale. Culture data pooled from cultures performed in triplicate (n>3 per culture). Error bars represent SD.

To better understand the suitability of HAMC as a cell delivery vehicle, cell distribution was studied and imaged by confocal reconstruction of a single cell suspension of RSPCs at 37° C. after 6 days of culture. Following 7 days of primary culture of actin-GFP retinal stem/progenitor cells, spheres were dissociated into a single cell suspension in a manner identical to pre-transplantation cell preparation, and distributed uniformly in HAMC. As shown in FIG. 4, RSPCs were homogeneously (and stably) distributed within the HAMC matrix unlike the distribution in media where cell aggregation was evident. This demonstrates that HAMC prevents cellular aggregation, which may be important for cell integration in the host tissue [Redenti S, Neeley W L, Rompani S, Saigal S, Yang J, Klassen H et al. *Engineering retinal progenitor cell and scrollable poly(glycerol-sebacate) composites for expansion and subretinal transplantation. Biomaterials* 2009; 30:3405-14]. Single cells are more easily injected through a fine needle without the risk of clogging the injection system than cell aggregates or spheres. Single cells have the potential advantage of better integration with host tissue. Thus, the cell delivery system developed here overcomes both pre-injection and post-injection cell distribution limitations by stably suspending cells. Notwithstanding these potential advantages of injections of dissociated cells, there may be advantages of delivering cell aggregates or cell spheres due to potentially greater viability as a result of more cell-cell interactions.

Forebrain-Derived Neural Stem Cells

Neurospheres were centrifuged and washed once in basic media. A small sample of neurospheres were triturated into single cells and counted with a hemacytometer using trypan blue (Sigma-Aldrich) exclusion to determine the starting live cell population. Dissociated single cells were cultured for 7 d. $2 \times 10^4$ NSPCs were dispersed in 100 µl of media alone or HAMC and then loaded into 1 ml syringes and injected through 30 G, 1" needle into black clear-bottom 96-well plates (Greiner™, Germany). Cells were imaged on an inverted microscope (Axiovert S100™, Zeiss) equipped with a camera (Cool SNAP HQ™, Photometrics) on day 2.

Figure 5:
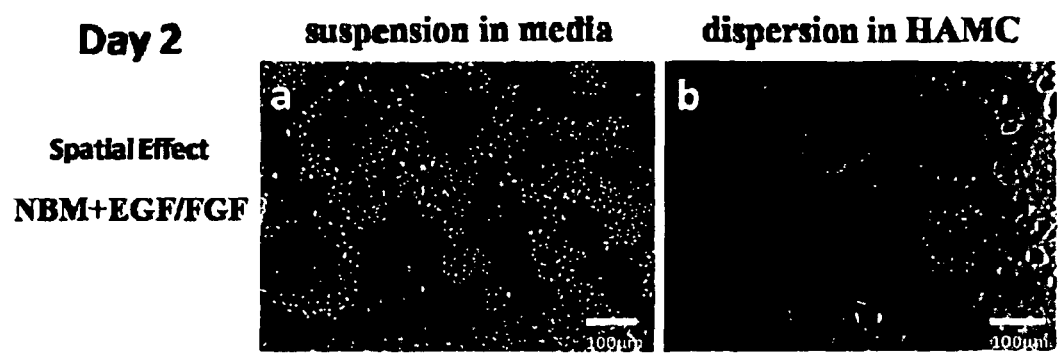
FIG. 5 illustrates bright-field microscopic images of NSPC neurosphere cultures at day 2: (a) cells cultured in proliferation media aggregated whereas those cultured in (b) proliferation media in HAMC remained dispersed throughout the gel.
Figure 6A:
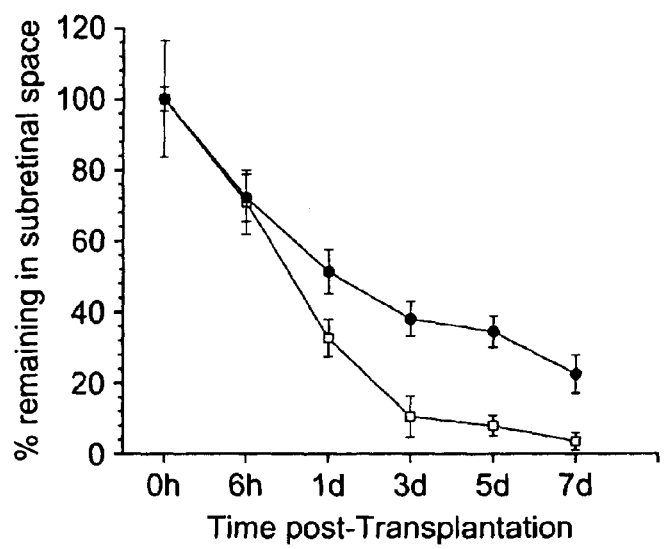
FIG. 6 illustrates in vivo characterization of HAMC degradation in the subretinal space. (a) Mass loss curves (% remaining) of HA (open circles) and MC (closed circles) over 7 days as assessed by confocal microscopy of fluorescently-labelled components (n=4 eyes analyzed per time point). Representative images from (b, c) HA and (d, e) MC degradation time courses. Confocal reconstructions are over an area of 1.3×1.3 mm of tissue, with tissue thickness (t) as indicated. Note the punctate appearance throughout the HA component within 6 hours of injection compared to MC.
Figure 6B:
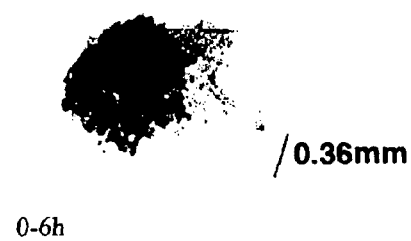
Figure 6C:
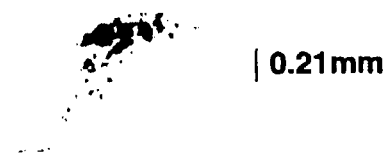
Figure 6D:
Figure 6E:

NSPCs cultured in media were compared to those cultured in HAMC in terms of cell distribution over time. As shown in bright-field images (FIG. 5), NSPC neurospheres cultured in proliferation media of EGF/FGF2/heparin alone aggregated (FIG. 5*a*) whereas those cultured in differentiation media in HAMC remained dispersed in the gel (FIG. 5*b*).

Example 2

Application of HAMC for Subretinal Injection

1. Evaluation of Degradation of Polymer Matrix In Vivo

The degradation profile of HA and MC was followed in vivo by measuring the fluorescence intensity over time. Fluorescently labeled HAMC was injected in the subretinal space (5 µL, 0.5/0.5 w/w %), as described in more detail in the transplantation protocol below. At t=0, 6 hours, 1, 3, 5, and 7 days after injection, animals were administered a lethal IP injection of sodium pentobarbital. To ensure the integrity of the neural retina and subretinal space, animals were perfused transcardially with saline and then 2% paraformaldehyde (PFA) immediately after sacrifice. Eyes were removed and placed in cold artificial cerebrospinal fluid (aCSF). Confocal image analysis using an Olympus Fluoview FV1000™ microscope was performed on whole eyes with the cornea-lens-retinal axis perpendicular to the laser scanning direction to minimize refraction from the lens. This was used to obtain three-dimensional reconstructions of the HA and MC in their native conformations post-injection in the subretinal space. The eyes were then dissected to remove autofluorescent extraocular muscle, as well as lens and vitreal attachments leaving only the posterior structures (neural retina and opposed RPE-choroid-sclera) undisturbed. Subsequent epifluorescent and confocal imaging confirmed localization of HAMC to the subretinal space, and confocal image analysis software (Fluoview V2.0b™) was used to quantify fluorescence intensity. Loss of fluorescence intensity per unit area was used as a measure of degradation for the HA and MC components. Values were corrected for background autofluorescence using non-injected tissue.

The in vivo degradation profile of HAMC (0.5/0.5) was followed by measuring the depletion in fluorescence intensity of fluorescently tagged Alexa Fluor 488-HA™ and Alexa Fluor 568-MC™ over 7 days. The fluorescently tagged HAMC composition was injected into the subretinal space of adult albino mice (see below) and visualized by confocal microscopy immediately after injection and then over time to determine the degradation profile (FIG. 6).

Fluorescence was quantified and normalized to day 0 controls using image analysis software. Both HA and MC exhibited rapid degradation within the first 6 hours after transplantation. HA exhibited a more rapid degradation over time, dropping to approximately 10% of initial levels within 3 days and falling to a minimum of approximately 3% after one week. In contrast, MC showed persistence within the subretinal space to approximately 20% of its initial value after 7 days. This provides evidence for the bioresorbability of the cell delivery vehicle in host tissue. While the rate of bioresorbability may change depending on the injection site in the body, the HAMC will be resorbable in the body regardless of the site of injection in the body, CNS or otherwise.

2. Transplantation of Retinal Stem Cells and Progeny in HAMC to the Subretinal Space Subretinal transplantation into the mouse eye was adapted from the technique described previously by Coles et al. [Coles B L K, Angenieux B, Inoue T, Rio-Tsonis K, Spence J R, McInnes R R et al. *Facile isolation and the characterization of human retinal stem cells. Proc Natl Acad Sci USA* 2004; 101:15772-7]. GFP$^+$ RSPC spheres were dissociated into single cells with an enzymatic solution (trypsin 1.33 mg/mL, hyaluronidase 0.67 mg/mL, kynurenic acid 0.2 mg/mL, 0.5 mg/mL collagenase I, 0.5 mg/mL collagenase II, 0.1 mg/ml elastase, Sigma Aldrich, Oakville, ON). The cells were resuspended in either MSS or 0.5/0.5 w/w % HAMC to a concentration of 10,000 cells/µL. Animals were brought to a surgical plane of anesthesia with isoflurane. Using a 34 gauge beveled needle attached to the Nanofil™ submicroliter injection system (World Precision Instruments, Sarasota, Fla.) 1 µL of cell suspension was injected into the subretinal space of adult CD10/Gnat2$^{-/-}$ using a Möller Hi-R 900C™ surgical microscope (Innova Medical Ophthalmics, Inc., Toronto, ON). Four weeks after transplantation, animals were sacrificed and transcardially perfused with saline followed by 4% PFA. The eyes were removed and stored in 4% PFA (4° C. for 4 hours), which was replaced with a 30% sucrose cryoprotectant solution (4° C. overnight). Tissue was placed in tissue fixative (FSC22™ Frozen Section Compound; Richmond, Ill.) and frozen overnight at −80° C. Frozen blocks were sectioned in a cryostat (−20° C.) at a thickness of 15 µm and mounted on Superfrost Plus Gold™ slides (Fisher Scientific, Ottawa, ON). Slides were then washed with Hoescht nuclear stain (Invitrogen, Burlington, ON) and reviewed by epifluorescence (ZeissAxio Observer.D1™) to observe GFP$^+$ cells. The percentage of Bruch's membrane covered by GFP$^+$ transplanted cells integrated along the RPE was quantified using fluorescence intensity analysis in ImageJ.

To evaluate the utility of HAMC for cell delivery, primary culture RSPCs isolated from beta-actin-GFP transgenic mice were dissociated to single cells and injected into the subretinal space of adult CD10/Gnat2$^{-/-}$ mice at a concentration of 10,000 cells/µL in either HAMC or saline alone. Mutation of the Gnat2 gene leads to cone dysfunction and progressive loss, which is a predictive and reliable measure of AMD severity [Bathos, B. G., Clarke, L., Coles, B. L. K., Cooke, M. J., Shoichet, M. S., van der Kooy, D. *A bioengineered delivery strategy improves the transplantation of retinal stem cells and differentiated progeny. Program No. 737.16. 2010 Neuroscience Meeting Planner. Washington, D.C.: Society for Neuroscience.* San Diego, Calif., Nov. 13-17, 2010].

Figure 7A:
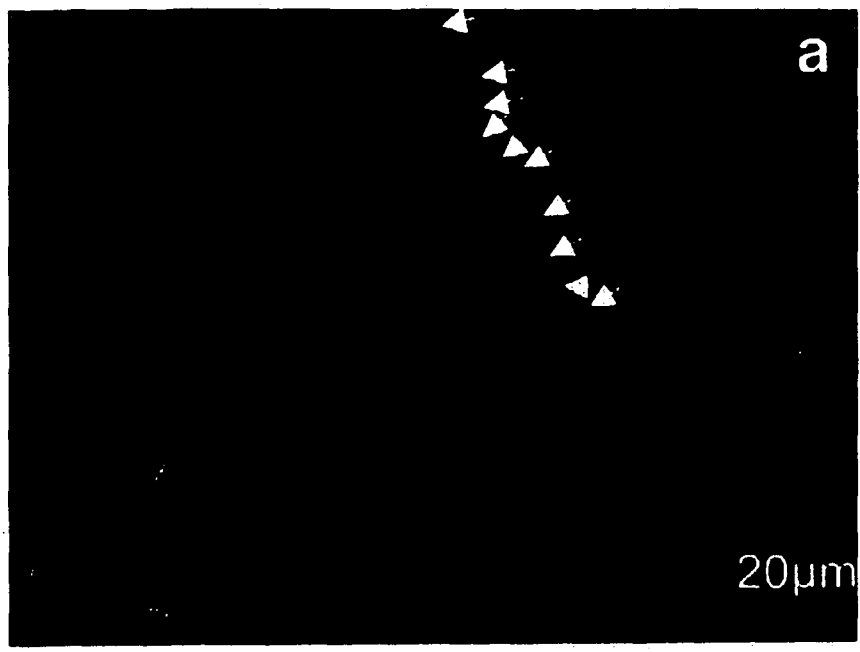
FIG. 7 illustrates in vivo adult subretinal transplantation of GFP$^+$ RSPCs in HAMC, assayed at 4 weeks post-transplantation. (a) Control transplantation in saline vehicle shows non-contiguous cellular integration and localized cellular groupings (inset) atop Bruch's membrane (BM), suggestive of cellular aggregation pre- or post-transplantation. (b) Transplantation in HAMC shows contiguous areas of RPE integration over large areas of retina (inset), suggesting HAMC maintains cellular distribution during injection and preventing aggregation pre- or post-transplantation. Arrowheads indicate location of nuclei of transplanted cells. Confocal images of cuboidal RPE cells sitting atop Bruch's membrane after injection in (c) saline and (e) HAMC (c,e, Hoechst and GFP; d,f, merge with DIC to show cytoplasm). Note non-contiguous distribution in buffered saline vehicle versus HAMC. (g) Integration along the RPE shows significantly greater coverage of Bruch's membrane over integrated areas by GFP$^+$ cells delivered in HAMC versus buffered saline (n=3 eyes each).
Figure 7B:
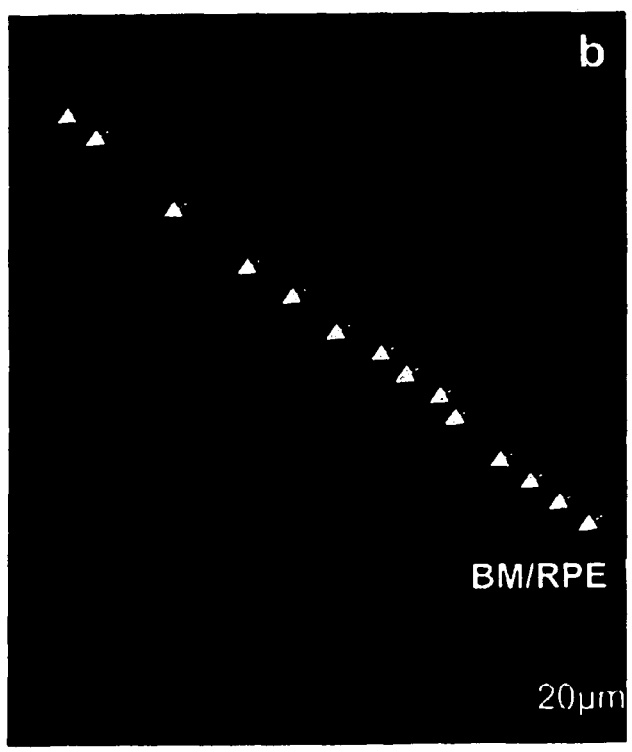
Figure 7C:
Figure 7D:
Figure 7E:
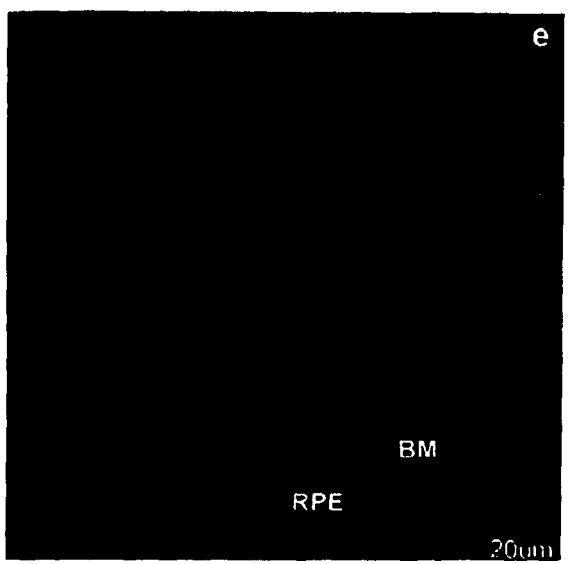
Figure 7F:
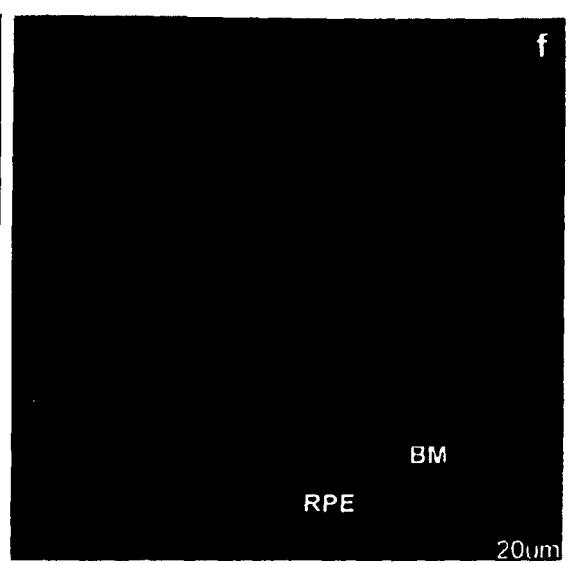
Figure 7G:
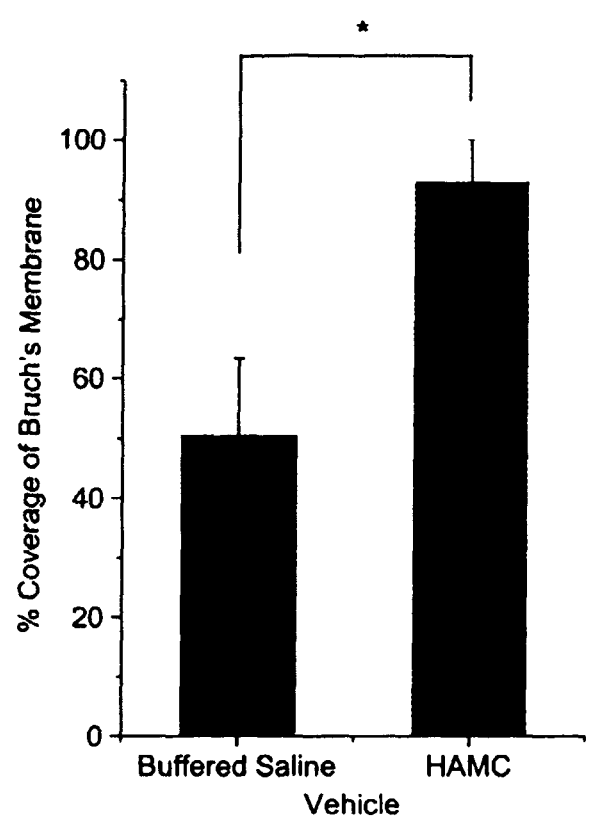

Tissue analysis at 4 weeks following injection revealed that RSPCs delivered in saline alone resulted in non-continuous banding patterns in the RPE (FIG. 7A). In contrast, RSPCs delivered in HAMC (0.5/0.5) integrated with the RPE and formed continuous banding patterns (FIG. 7B). The cellular morphology of the GFP-positive and nuclear-stained transplanted cells was consistent with the cuboidal epithelium characteristic of RPE cells, sitting atop Bruch's membrane (BM) (FIG. 7C-F). In order to quantify this increase in cellular distribution seen with HAMC, the percentage of Bruch's membrane covered by GFP+ cells was quantified using image analysis software. Delivery with HAMC resulted in a significant increase in coverage over buffered saline vehicle (FIG. 7G): 93% with HAMC vs. 50% with saline. Qualitatively, there was no observed effect of HAMC versus saline injection on retinal morphology in terms of overall thickness, laminar integrity or the appearance of the ONL and RPE/Bruch's membrane. This is further evidence for the ability to inject the vehicle without risk of host tissue damage that might arise during the placement of a solid, cell-seeded scaffold. The non-adhesive properties also serve to minimize scar formation. Taken together, delivering RSPCs in HAMC had a dramatic effect on cellular distribution within the host tissue, with a marked reduction in cellular aggregation and improved distribution over the RPE/Bruch's membrane. This cell delivery strategy may be useful for the treatment of widespread or advanced maculopathy, where large areas of the RPE are destroyed. The choroidal neovascularization inherent in wet-AMD is marked by widespread disruption of the RPE and disturbance of the homeostatic mechanisms of photoreceptor outer segment phagocytosis. The RPE replacement potential demonstrated by the cell delivery system is therefore therapeutically relevant to the treatment of AMD.

Example 3

Evaluation of HAMC for Spinal Cord Injury Repair

All studies were performed in adult female Sprague Dawley rats (n=9, 250-300 g; Charles River, St. Constant, Canada) in accordance with animal protocols approved by the Animal Care Committee of the Research Institute of the University Health Network. Animals were anesthetized by the inhalation of 2% halothane with 1:2 nitrous oxide and oxygen. A laminectomy was performed at the T8-T9 vertebral level, followed by a clip compression injury with a 27-g force for 1 min. [Ballios, B. G., Clarke, L., Coles, B. L. K., Cooke, M J., Shoichet, M. S., van der Kooy, D. *A bioengineered delivery strategy improves the transplantation of retinal stem cells and differentiated progeny. Program No.* 737.16. 2010 *Neuroscience Meeting Planner*. Washington, D.C.: Society for Neuroscience. San Diego, Calif., Nov. 13-17, 2010]. The wounds were then sutured and the rats allowed to recover for 14 days.

GFP-positive neurospheres were mixed in HAMC or Neurobasal media by vortexing ($1 \times 10^6$ cells in 5 µl total volume) and then transplanted into the injury site 14 days after the injury. Briefly, animals were anesthetized by halothane inhalation and the injury site was reopened and the dura exposed. Next, the neurosphere suspension (in HAMC or media) kept at 4° C. was drawn up into a 10 µl syringe (Model No: 7635-01; Hamilton, Reno, Nev., USA) attached to a manual microinjector through a customized needle (32 G and 20° bevel; Hamilton). The dura was pierced with a sterile 30-gauge needle at the intended site of injection. The customized needle was then inserted into the spinal cord with the aid of a surgical microscope through the hole previously created in the dura, and 5 µl of the cell suspension mixed in HAMC or media was injected over 2 min directly into the clip injury site. The needle was left in place for 2 min after injection prior to withdrawal to minimize cell leakage. A total of 8 rats were used for the 2 treatment groups, NSPCs in HAMC (n=4) and NSPCs in media (n=4). All animals received cyclosporine daily subcutaneously (15 mg/kg, Sandimmune™, Nacartis Pharma Canada Inc., Dorval, QB, Canada) for the duration of the experiment to aid transplant survival.

Seven days after cell transplantation, rats were sacrificed by an intraperitoneal injection of 1.0 ml of sodium pentobarbital. The spinal cord was removed and an 8 mm length section (encompassing approximately 1 mm rostral and caudal to injury site) was carefully excised. Cell survival was assayed using Fluorescence Activated Cell Sorting (FACS).

Spinal cord tissue (1 mm rostral and caudal to injury site) was removed and digested with papain to get a single cell suspension. The resulting cell suspension was passed through a cell strainer (40 µm, BD Biosciences, Bedford, Mass., USA) to remove cell aggregates. GFP-positive neurospheres dissociated into a single cell suspension and non-transplanted spinal cord tissue, were used as positive and negative controls respectively. Fluorescence Activated Cell Sorting (FACS) was performed for the separation of cells based on GFP expression and Propidium Iodide (PI) uptake. PI is an indicator of dead cells hence PI-negative/GFP-positive cell counts were determined for each sample using the FACSArray Bioanalyzer System™ (BD Biosciences, Mississauga, ON, Canada). The fluorochromes were excited with FACSArray Bioanalyzer™ standard 488-nm laser, GFP was detected using 530/30 filter and PI was detected using the 675/20 filter. A 100-µm ceramic nozzle (BD Biosciences), sheath pressure of 20-25 PSI, and an acquisition rate of 1,000-3,000 events were used as conditions optimized for NSPC sorting. Data was analysed with FACSDiva™ (BD Biosciences) and FlowJo™ software (Tree Star, Ashland, Oreg., USA).

To determine if HAMC enhances cell survival in vivo, NSPCs were transplanted into rats after clip compression SCI and assayed for cell survival at 7 days post-transplantation. The clip compression injury model was used because of its clinical relevance to human disease/injury [Kunishima, M; Kawachi, C.; Morita, J.; Terao, K.; Iwasaki, F.; Tani, S. *4-(4,6-dimethoxy-1,3,5-triazin-2-yl)-4-methyl-morpholinium chloride: an efficient condensing agent leading to the formation of amides and esters. Tetrahedron* 1999; 55; 13159-13170; Ellman, G. D. *Tissue sulfhydryl groups. Archives of Biochemistry and Biophysics* 1959; 82; 70-72; Coin, L; Beyermann, M; Bienert, M *Solid-phase peptide synthesis: from standard procedures to the synthesis of difficult sequences. Nature Protocols* 2007; 2; 3247-3256]. NSPCs used in this study were isolated from GFP transgenic rats to enable the identification of donor cells based on fluorescent marker expression. FACS showed enhanced survival of GFP+NSPCs after 7 days in vivo, in the animals that were transplanted with cells mixed in HAMC (n=3) compared to cells suspended in media (n=3). GFP expression and Propidium Iodide (PI) uptake were used for cell sorting and the resultant PI-negative/GFP-positive cell counts showed that approximately twice as many cells were present at 7 days post-SCI in the HAMC animals ($3.88 \pm 0.52 \times 10^5$ cells; $39 \pm 15\%$ of transplanted GFP+NSPCs) versus the media controls ($1.90 \pm 0.54 \times 10^5$; $19 \pm 5\%$ of transplanted GFP+NSPCs). These results suggest that HAMC provides some protection to the transplanted cells against the hostile milieu that result after SCI. This two-fold increase in cell survival is statistically significant and may translate to enhancement of regeneration in the injured spinal cord and ultimately to functional recovery. In on-going studies, we are examining ways to further enhance in vivo survival of NSPCs after SCI with our novel cell delivery system and to investigate the effect of HAMC on their differentiation both in vitro and in vivo.

Example 4

Biomaterial Screening and Selection

RSCs were derived from the ciliary epithelium of adult ACTB-GFP or -YFP mice as described previously [Inoue, T, Coles, B. L., Dorval, K, Bremner, R., Bessho, Y, Kageyama, R., Hino, S., Matsuoka, M, Craft, C. M, McInnes, R. R., Tremblay, F., Prusky, G. T., and van der Kooy, D. *Maximizing functional photoreceptor differentiation from adult human retinal stem cells. Stem Cells* 2010; 28; 489-500]. Cells were plated in SFM on non-adherent tissue culture plates (Nunc™; Thermo Fisher Scientific, Rochester, N.Y.) at a density of 20 cells/µL. Floating spheres of cells grew from the clonal proliferation of single pigmented retinal stem cells to give rise to pigmented RPE progenitors and non-pigmented neural retinal progenitors, the second of which could differentiate into all retinal neuronal and glial subtypes [Tropepe V. Coles B L K, Chiasson B J, Horsford D J, Elia A J, McInnes R R et al. *Retinal stem cells in the adult mammalian eye. Science* 2000; 287:2032-36; and Coles B L K, Angenieux B, Inoue T, Rio-Tsonis K, Spence J R, McInnes R R et al. *Facile isolation and the characterization of human retinal stem cells. Proc Natl Acad Sci USA* 2004; 101:15772-7].

Following 7 days of primary culture, spheres were either mixed directly with hydrogels reconstituted in growth media, or dissociated into a single cell suspension in a manner identical to pre-transplantation cell preparation (see below). Survival was assayed using fluorescence imaging and single cell counting, with ethidium homodimer-1 (EthD-1, 10 µM final concentration) (Invitrogen, Burlington, ON) used to mark dead cells. Proliferation was assayed by measuring the sphere diameter over 6 days of culture in the biomaterial matrix. Staining and fluorescence was visualized using a ZeissAxio Observer.D1™ inverted fluorescent microscope equipped with an AxioCamMRm™ digital camera, and imaged using ZeissAxioVision™ V4.6 software. Significance is noted only if $p<0.05$, as determined by using standard Student's t-test.

Figure 8A:
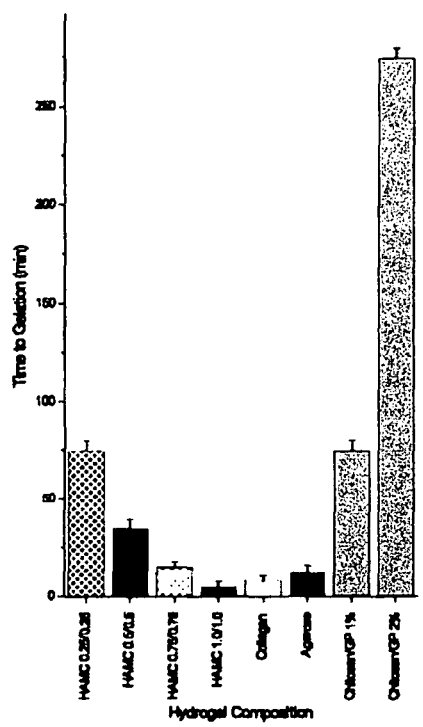
FIG. 8 illustrates screening results to determine the optimal biomaterial for cell delivery to the retina, with the following naturally-derived polymers that met the initial criteria of biodegradability, biocompatibility and injectability through a 34 gauge needle (85 μm inner diameter): HAMC, agarose, collagen, and chitosan/GP. These biomaterials were compared in terms of time to gelation and cellular response.

In order to determine the optimal biomaterial for cell delivery to the retina, we screened the following naturally derived polymers that met our initial criteria of biodegradability, biocompatibility and injectability through a 34 gauge needle (85 µm inner diameter): HAMC, agarose, collagen, and chitosan/GP. These biomaterials were compared in terms of time to gelation and cellular response. A material that gelled between 10 and 60 minutes, using the simple inverted tube assay, was thought to be suitable in terms of handling in vitro and cell delivery in vivo, providing sufficient time for cell loading in vitro and cell distribution in vivo prior to gelation. Of the biomaterials tested, all met our time to gelation criterion except the chitosan/GP formulations (1% and 2%) and the weakest HAMC physical blend (0.25/0.25 w/w %, FIG. 8*a*). Of the HAMC physical polymer blends, the 0.5/0.5 and 0.75/0.75 w/w % passed the injectability screen. Higher weight percentages were not injectable through the 34 gauge needle, and were not considered further.

Figure 8B:
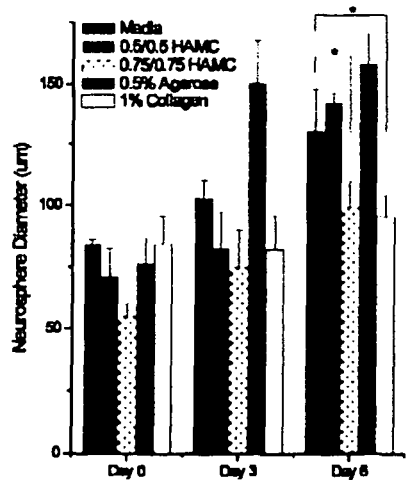
Figure 8C:
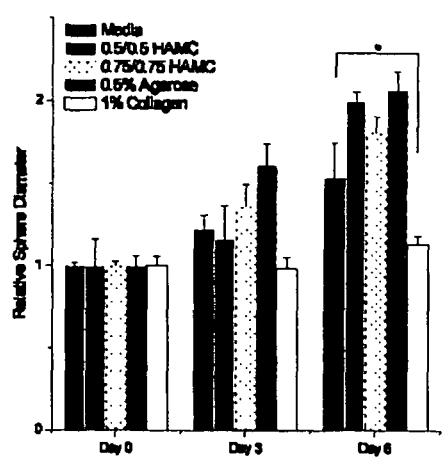
Figure 8C:
Figure 8F:
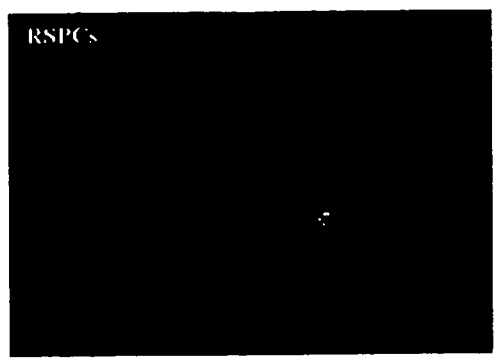

HAMC (0.5/0.5 and 0.75/0.75 w/w %), agarose and collagen were evaluated in terms of cellular response with cells cultured within each hydrogel and specifically in terms of RSPC growth in vitro relative to media controls. As RSPCs are normally cultured as spheres, sphere diameter was used as a proxy for cell growth with care taken to exclude the influence of sphere aggregation, as described further below. As shown in FIG. 8*b* and *c*, RSPC spheres increased in diameter in HAMC 0.5/0.5 similar to media controls. In HAMC 0.75/0.75, spheres increased in relative diameter similar to media controls, but did not reach the same absolute diameter after 6 days. Sphere mixing in HAMC 0.75/0.75, due to its higher viscosity, consistently resulted in reduced initial sphere diameter due to loss of cells from outer layers. Interestingly, sphere growth in collagen lagged significantly behind control growth media conditions in both absolute and relative diameter, and thus collagen was not pursued further. While the RSPC spheres grew to significantly higher diameters in agarose, the growth was characterized by cell spreading and morphological differentiation (FIG. 8*f*), suggesting loss of multipotency. Thus, agarose was removed from further consideration. In contrast, spheres plated in HAMC formulations exhibited similar relative growth as in media controls, but without cell spreading (FIG. 8*b-e*). Thus, further studies were pursued with HAMC 0.5/0.5 and 0.75/0.75.

Figure 8G:
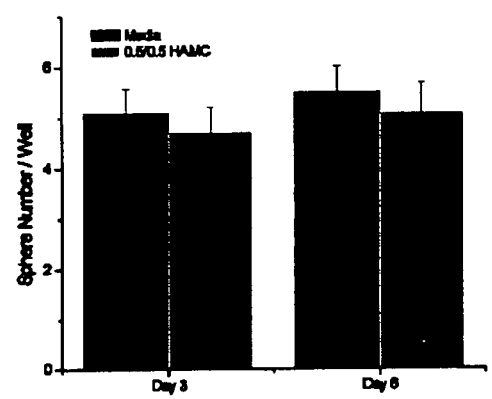

It has been demonstrated that increases in primary RSPC sphere diameter can take place through two processes: proliferative cell division [Ballios, B. G., Cooke, M J., Clarke, L., Coles, B. L. K, Shoichet, M. S., van der Kooy, D. *Bioengineered delivery system for the transplantation of mouse adult retinal stem cells. Control No.* 321. 2010 ISSCR Meeting Planner. Deerfield, Ill.: International Society for Stem Cell Research, 2010. San Francisco, Calif., Jun. 16-19, 2010] and aggregation and merging of smaller spheres [Ballios, B. G., Clarke, L., Coles, B. L. K, Cooke, M J, Shoichet, M. S., van der Kooy, D. *A bioengineered delivery strategy improves the transplantation of retinal stem cells and differentiated progeny. Program No.* 737.16. 2010 Neuroscience Meeting Planner. Washington, D.C.: Society for Neuroscience. San Diego, Calif., Nov. 13-17, 2010]. In order to separate these two phenomena and validate the sphere diameter assay as a measure of proliferation, individual spheres were counted (FIG. 8G). Approximately 5 spheres per well chosen from primary cultures were plated in HAMC and control media, and counted over 6 days. There was no change in the number of spheres per well, indicating that cells were proliferating rather than spheres coalescing. For the latter to have been true, the number of spheres would have decreased.

Example 5

Evaluation of Direct Survival Effect of HAMC on Retinal Stem Cell-Derived Cell Types In Vitro There is increasing evidence that partially differentiated, post-mitotic cell types may yield improved integration into host tissue after transplantation. Studies using embryonic photoreceptors have demonstrated functional integration in retina of adult mice [MacLaren, R. E., Pearson, R. A., MacNeil, A., Douglas, R. H., Salt, T. E., Akimoto, M., Swaroop, A., Sowden, J. C., and Ali, R. R. *Retinal repair by transplantation of photoreceptor precursors. Nature* 2006; 444; 203-207]. However, only 10% of differentiated RSC progeny produce rod photoreceptors when cultured in serum. Although viral transfection of retinal stem cells (RSCs) with three photoreceptor-inducing transcription factors can increase the number of photoreceptors to over 50% of all progeny [Inoue, T, Coles, B. L., Dorval, K., Bremner, R., Bessho, Y, Kageyama, R., Hino, S., Matsuoka, M., Craft, C. M, McInnes, R. R., Tremblay, F., Prusky, G. T., and van der Kooy, D. *Maximizing functional photoreceptor differentiation from adult human retinal stem cells. Stem Cells* 2010; 28; 489-500], this is not a clinically feasible approach due to the concern regarding insertional mutagenesis. We have found that a combination of taurine and retinoic acid added to differentiating RSC colonies can greatly increase the numbers of rod photoreceptors to over 80% of all progeny [Ballios, B. G., Cooke, M J., Clarke, L., Coles, B. L. K., Shoichet, M. S., van der Kooy, D. *Bioengineered delivery system for the transplantation of mouse adult retinal stem cells. Control No. 321. 2010 ISSCR Meeting Planner*. Deerfield, Ill.: International Society for Stem Cell Research, 2010. San Francisco, Calif., June 16-19; and Ballios, B. G., Clarke, L., Coles, B. L. K., Cooke, M J., Shoichet, M. S., van der Kooy, D. *A bioengineered delivery strategy improves the transplantation of retinal stem cells and differentiated progeny. Program No. 737.16. 2010 Neuroscience Meeting Planner*. Washington, D.C.: Society for Neuroscience, 2010. San Diego, Calif., Nov. 13-17, 2010].

Figure 9A:
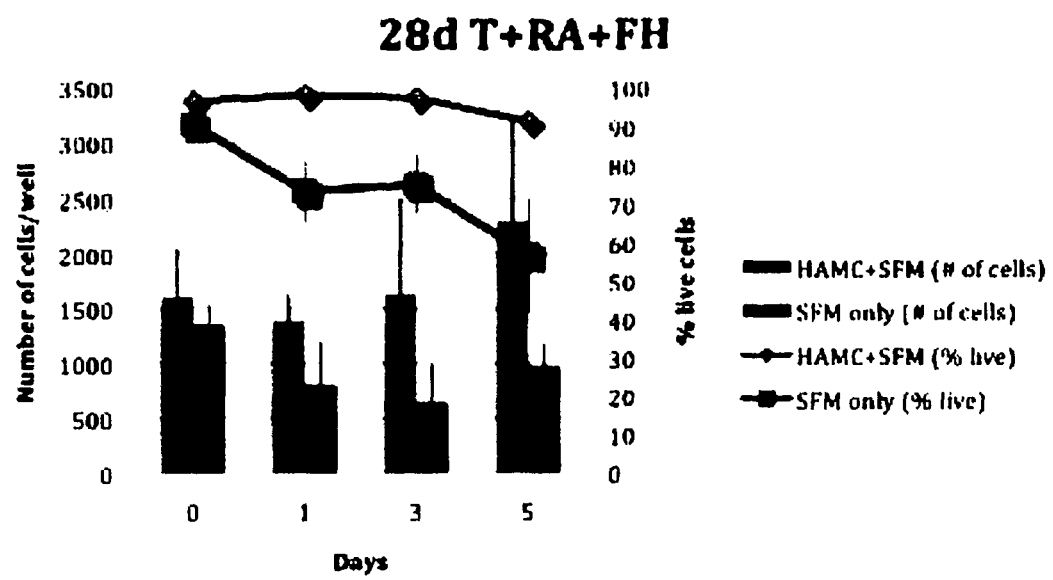
FIG. 9 illustrates direct survival effect of HAMC on RSC-derived post-mitotic retinal cells over 5 days in vitro. (A) Pre-differentiated RSC-derived rod photoreceptors (28 d in taurine/retinoic acid (T+RA) and FGF2/heparin (F/H)) show significantly higher viability when cultured in the presence of HAMC and serum free media (SFM) than SFM alone. (B) They maintain their mature rod phenotype, as shown by rhodopsin expression.
Figure 9B:
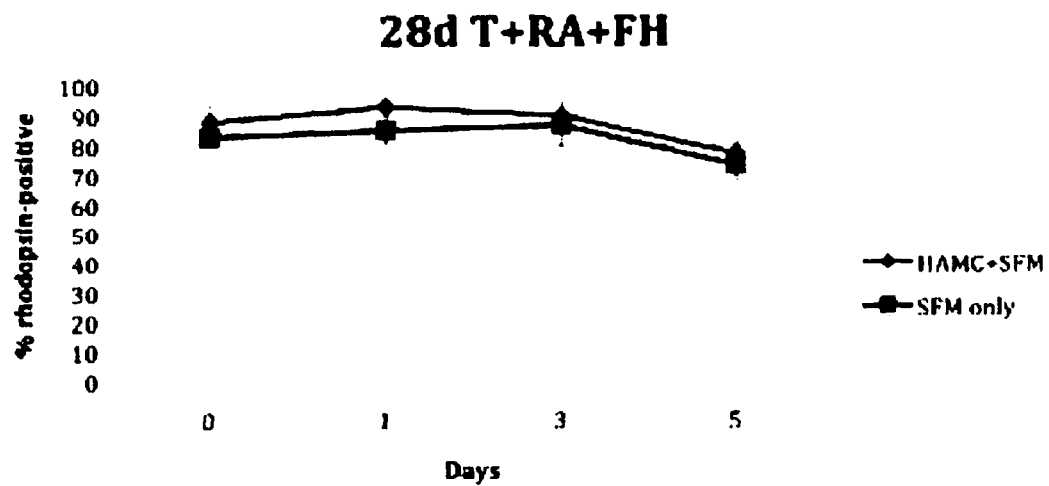

To better understand the direct effects that HAMC might have on encouraging the survival of a pre-differentiated RSC-derived retinal cell type, cell survival and phenotype was studied on pre-differentiated RSC-derived post-mitotic cells. RSC progeny were pre-differentiated in vitro for 28 days on laminin substrate in the presence of either taurine/retinoic acid (photoreceptor-induction media) or 1% fetal bovine serum (pan-retinal cell type induction media). At 28 days, induction factors were removed and the cells were exposed to either HAMC reconstituted in serum free media (SFM), or SFM alone for 5 days. Survival was assessed with ethidium homodimer (as previously described) and phenotype by immunocytochemical staining for Pax6, RPE65, and rhodopsin (Pax6, 1:400, Developmental Studies Hybridoma Bank; RPE65, 1:250, Millipore; RetP1, 1:250, Millipore). It was found that the post-mitotic photoreceptors showed significantly improved survival over 5 days in HAMC relative to media alone (FIG. 9A), with no change in mature photoreceptor phenotype as determined by rhodopsin expression (FIG. 9B).

Given the important role that a post-mitotic RSC-derived cell population might play in cell therapy in the retina, a direct effect of HAMC on improving cell survival is another advantage of HAMC as a cell delivery vehicle.

Example 6

Evaluation of Direct Survival Effect of HAMC on Retinal Stem Cell-Derived Photoreceptors Following Transplantation In Vivo In addition to improving cellular distribution of undifferentiated RSC progeny across the RPE layer of the retina following transplantation, we have studied the effect of HAMC on survival of RSC derived photoreceptors following transplantation into adult retina. Based on our studies of photoreceptor induction from RSCs, 12 days in culture with taurine/retinoic acid yields a cell population predominantly composed of early post-mitotic rod photoreceptors (Nrl-positive, rhodopsin-negative) [Ballios, B. G., Clarke, L., Coles, B. L. K, Cooke, M J., Shoichet, M. S., van der Kooy, D. *A bioengineered delivery strategy improves the transplantation of retinal stem cells and differentiated progeny. Program No. 737.16. 2010 Neuroscience Meeting Planner*. Washington, D.C.: Society for Neuroscience, San Diego, Calif., Nov. 13-17, 2010]. These pre-differentiated cells were transplanted into the subretinal space of adult mice (1 µL injection, 10,000 cells/µL). In both saline and HAMC vehicles, these cells were transplanted with a transiently acting glial toxin (alpha-aminoadipic acid) to eliminate the glial outer limiting membrane present in adult retina, and enhance cellular integration. Injection of cells in HAMC yielded significantly increased survival relative to injection in saline vehicle alone (HAMC: 330±90 cells, saline: 117±30, p<0.05, N=3).

Example 7

Delivery of Cells in HAMC to the Brain

Following stroke there is a reduction in nutrients and oxygen to cells in the brain, resulting in cell death. Transplantation is proposed as a method to replace the lost and damaged cells. Direct injection(s) into the brain presents a method to locally deliver cells to the site of injury. Injections into tissue are problematic due to resistance to the injection volume. This resistance results in "back-flow" where the injection medium does not remain in the tissue and flows along the path of least resistance i.e. back up the needle track. Back-flow of the injection volume carries the transplanted cells back up the needle tract and onto the external surface where the needle entered the tissue, thus reducing the numbers of cells delivered to the tissue. By co-transplanting cells in a HAMC upon injection into the tissue a gel will be formed and prevent back-flow.

Fluorescent cells YFP murine neural stem/progenitor cells were suspended in HAMC for injection. Neural stem/progenitor cells were dissociated into single cells and counted to determine the cell number. Cells were centrifuged to remove media and re-suspended in aCSF to a final volume of 10 µL. Cells were mixed with a 1%:1% MC:HA solution made in aCSF to yield a cell suspension in a total volume of 204. Cells were kept on ice until required for injection. A mouse was placed in a sterotaxic frame, an incision made and a hole drilled in the skull 0.4 posterior to bregema, 2.25 lateral to the midline. Cells were loaded into a 26 G needle with a 45° bevel on a Hamilton 10 µL gas tight syringe. 0.5 µL of cells were expelled from the needle to confirm loading and the needle was placed in a sterotaxic and placed 1.0 below the surface of the brain. Cells were injected at a rate of 0.14 per minute for a total volume of 0.54. The needle was left in place for 10 minutes and withdrawn at a rate of 0.2 mm per minute. The animal was sutured and allowed to recover.

To analyse the data animals were sacrificed 0 days, 3 days and 7 days following injection. Brains were removed and posted-fixed in 4% PFA. Cells were fixed in 4% PFA for 1 day and cryoprotected in 30% sucrose in ddH$_2$O (w/w) until brains sink. Brains were frozen in dry ice cooled 2-methyl butane and cryosectioned to 30 µm. To visualise cells anti-GFP antibody with corresponding secondary was used according to standard staining protocols. Cells were imaged using a fluorescent microscope. To assess cell distribution low magnification images were taken. These images show where the cells are located in the transplantation site.

Figure 10:
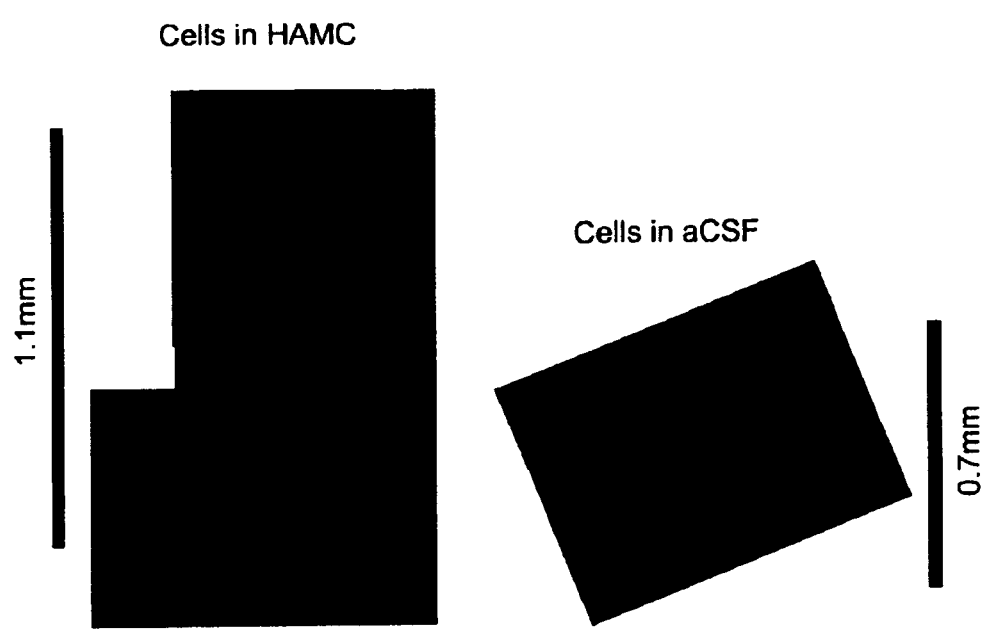
FIG. 10 illustrates cells transplanted in HAMC remain distributed throughout the injection site. Seven days after transplantation cells in aCSF are mainly located at the surface of the injection site. In contrast cells transplanted in HAMC can be found throughout the injection site.

Immediately after transplantation, when cells were co-transplanted in HAMC back-flow of the injection medium was reduced. Cells transplanted in HAMC were found in the brain tissue at the site on injection. In contrast when cells were transplanted in a solution, e.g. aCSF back-flow is seen and cells become located on the surface of the brain and not in the tissue. This back-flow phenomenon is observed following 7 days in vivo by a layer of the transplanted cells being located at the periphery of the injection site (FIG. 10). When cells were transplanted in HAMC 7 days following injection an even distribution of cells was observed throughout the needle tract with numerous cells remaining in the tissue (FIG. 10).

Example 8

In Vitro Characterization of Four HAMC Blends

The in vitro characteristics of four HAMC blends (0.5/0.5, 0.75/0.75, 0.75/1.0, 1.0/1.0) were investigated to assess their suitability for cell delivery. Yield stress and gelation point were measured as functions of polymer content and cell loading using flow and oscillatory rheology. Cell distribution and viability were examined via confocal reconstruction and live/dead staining. These experiments illustrate how the composition of HAMC affects its properties.

Figure 11:
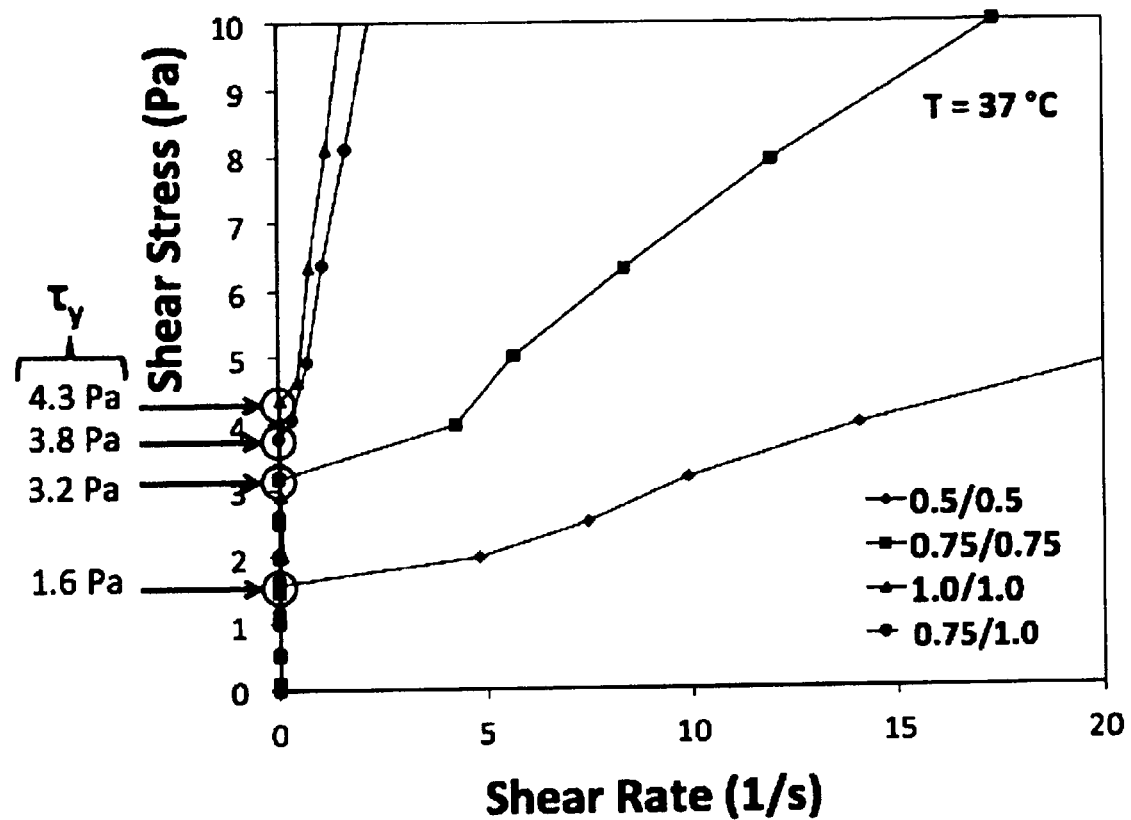
FIG. 11 illustrates shear stress vs. shear rate relationship for four HAMC blends without cells (0.5/0.5, 0.75/0.75, 0.75/1.0, 1.0/1.0) demonstrating yield stresses ($\tau_y$) that increase with total polymer content.
Figure 12:
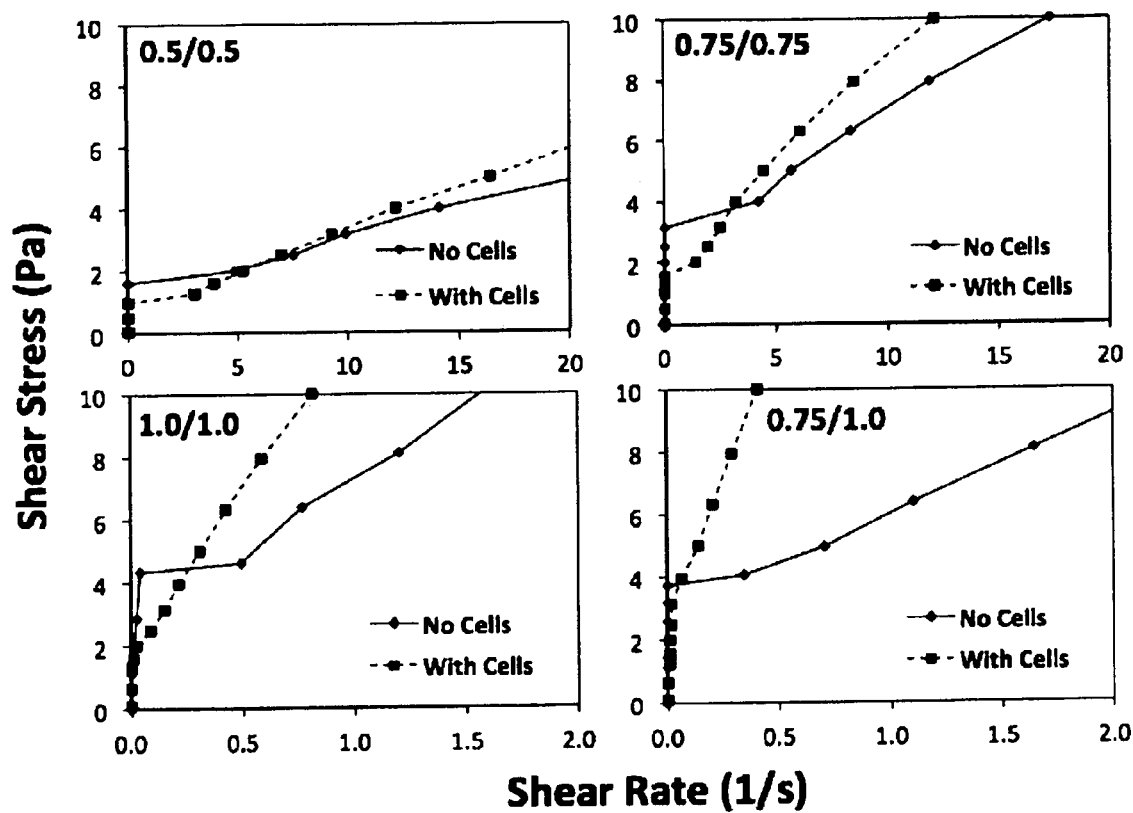
FIG. 12 is a comparison of shear stress vs. shear rate relationship for four HAMC blends (0.5/0.5, 0.75/0.75, 0.75/1.0, 1.0/1.0) without cells and with 10 million cells per mL. For all blends, the presence of cells reduces, but does not eliminate, the yield stress.
Figure 13:
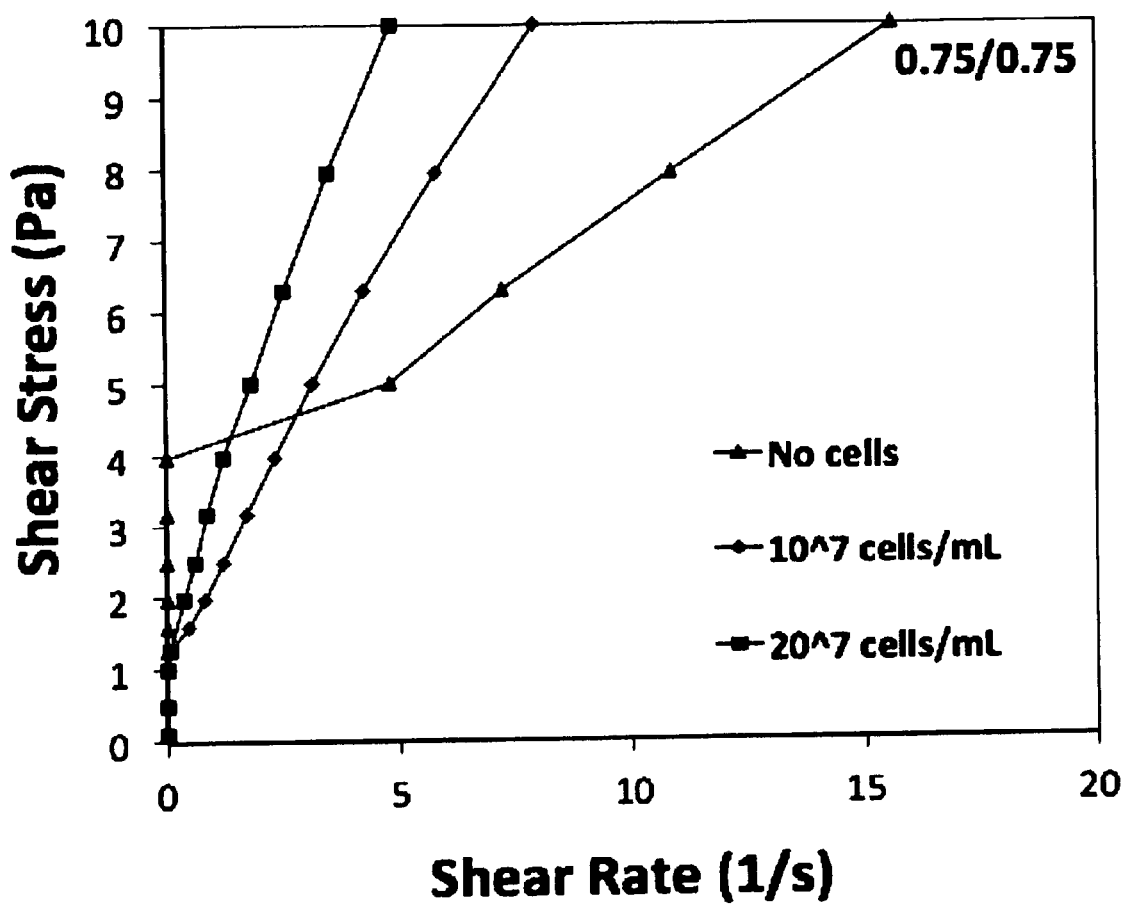
FIG. 13 illustrates the effect of cell loading on yield stress (0.75/0.75 HAMC blend). Yield stress is reduced to the same extent for loadings of 10 million and 20 million cells per mL.

HAMC blends were prepared as described in Example 1. All rheological data was collected using a TA Instruments AR 1000™ rheometer (New Castle, Del., USA) equipped with a 60 mm, 1° acrylic cone. Temperature was controlled using an integrated Peltier plate and sample evaporation was minimized using a solvent trap. HAMC yield stress was characterized via stress-controlled steady state experiments at 37° C. To allow for thermal equilibration, samples were conditioned for 20 minutes at 37° C. prior to shear. Shear rates were then recorded for shear stresses ranging between 0.01 and 20 Pa. FIG. 11 displays shear stress vs. shear rate data for the four blends without cells. The yield stress, given by the y-intercept, increased with total polymer content in the HAMC blend. This confirms that the gel is strengthened upon addition of both methylcellulose, which comprises the physical gel-forming crosslinks, and hyaluronan, which enhances gelation via viscosity and salting-out effects. Importantly, this shows that gel strength can be tuned through compositional adjustment. As is shown in FIG. 12, the addition of cells (at a loading of 10 million per mL) reduced the yield stress of all four blends. This indicates that the dispersion of cells throughout the polymer matrix results in a weaker gel, possibly by impeding the formation of hydrophobic junctions between methylcellulose chains. However, it does not prevent gelation entirely, as the yield stress remained non-zero for even the weakest HAMC blend. Furthermore, as shown in FIG. 13, the yield stress was the same for cell loadings of 10 million and 20 million per mL, revealing that at therapeutically relevant loadings the cell-mediated yield stress reduction is independent of the number of cells in the polymer matrix. Consequently, the ability of HAMC to form a gel is preserved after incorporation of cells into the blend.

Figure 14:
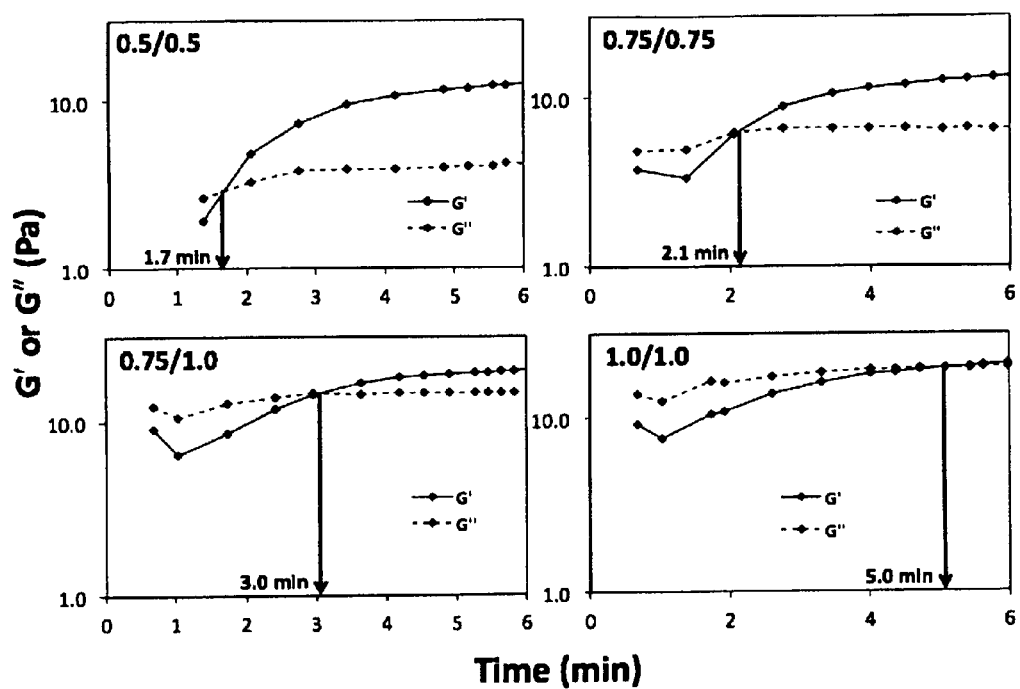
FIG. 14 illustrates the gelation point of four HAMC blends (0.5/0.5, 0.75/0.75, 0.75/1.0, 1.0/1.0). Storage (G') and loss (G") moduli were measured over time after temperature adjustment from 4 to 37° C. at time zero, simulating in vivo injection. Gelation time and moduli at the gelation point tended to increase with total polymer content, but all blends gelled in five minutes or less.

The gelation points of the HAMC blends were characterized via measurement of the storage (G') and loss (G") moduli as functions of time. To simulate in vivo injection, the temperature of the Peltier plate was changed from 4 to 37° C. at time zero and the moduli were recorded periodically for 40 minutes at an angular frequency of 1 Hz and 1% strain (which were confirmed to lie within the linear viscoelastic regions of the HAMC blends). The gelation point is defined as the time in which G' is equal to G". As shown in FIG. 14, gelation time and moduli at the gelation point tended to increase with total polymer content. This means that the gel, although it takes slightly longer to form, is stronger when there is more methylcellulose and hyaluronan in the blend, which is in agreement with the yield stress data presented in FIG. 11. Significantly, all blends formed a gel relatively quickly, as the slowest gelling blend required only 5 minutes to reach its gelation point.

Example 9

Chemical Modification of Methyl Cellulose for Peptide Conjugation

Figure 15A:
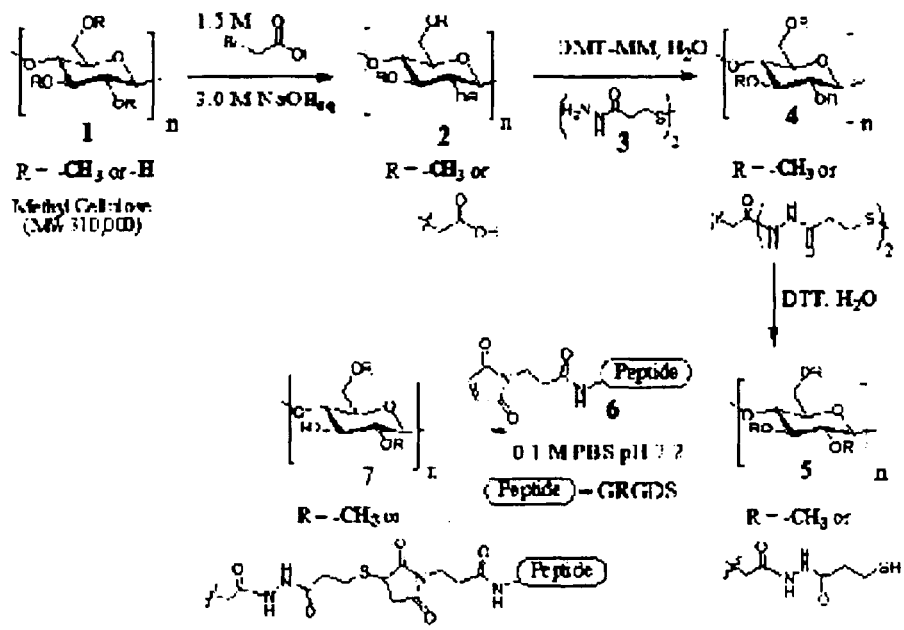
FIG. 15(A) is a synthetic scheme for the preparation of (7) via conjugation of peptides (6) to modified methylcellulose (5) and FIG. 15(B) shows results of amino acid analysis of peptide-conjugated MC (7).

Covalent conjugation of the desired peptide to methyl cellulose was achieved according to FIG. 15A. Methyl cellulose (MC, 1, MW 310 kg mol$^{-1}$, ShinEtsu Metolose SM-4000™, Japan) was chemically modified to its carboxylated derivative (carboxylated-MC, 2) using a previously described protocol [Hermanson, G. *Bioconjugate Techniques. Second edition*, San Diego, Calif.: Academic Press, 1996]. The product was purified by extensive dialysis (12 K-14 K MWCO) against 0.1 M NaCl and then distilled water. Dithiodipropanoic acid dihydrazide linker (3) was conjugated to carboxylated-MC (2) using the coupling agent 4-(4,6-dimethoxy-1,3,5-triazin-2-yl)-4-methylmorpholinium chloride (DMT-MM) in distilled water. MC derivative (4) was purified by dialysis against DI water [Kunishima, M; Kawachi, C.; Morita, J.; Terao, K; Iwasaki, F.; Tani, S. *4-(4,6-dimethoxy-1,3,5-triazin-2-yl-4-methyl-morpholinium chloride: an efficient condensing agent leading to the formation of amides and esters. Tetrahedron* 1999; 55; 13159-13170]. The disulfide linker was reductively cleaved using dithiothreitol (DTT) in water to afford sulfhydryl-MC (5). Purification was achieved using extensive dialysis with diluted HCl$_{aq}$ (pH 5), followed by DI water. Lyophilization was used to concentrate polymer (5). Quantification of free sulfhydryl groups present in 5 was achieved using Ellman's method and showed 430 µmol free sulfhydryl groups/g of 5±11 µmol/g. Cysteine was used for the standard calibration curve [Ellman, G. D. *Tissue sulfhydryl groups. Archives of Biochemistry and Biophysics* 1959; 82; 70-72].

RGD-peptide (6) was synthesized using conventional Fmoc chemistry via solid phase peptide synthesis on Wang resin with the sequence Gly-Arg-Gly-Asp-Ser. [4] After deprotection of the final amino acid, maleimido-propanoic acid was coupled to the N-terminus of the peptide by using di-isopropylcarbodiimide (DIC). The maleimido-containing peptide was cleaved using a solution of TFA/H$_2$O/TIS (90:5:5) for 2.5 hours [Coin, I.; Beyermann, M; Bienert, M. *Solid-phase peptide synthesis: from standard procedures to the synthesis of difficult sequences. Nature Protocols* 2007; 2; 3247-3256]. The solvents were evaporated under a stream of nitrogen, and the crude product was purified by reversed-phase HPLC (C-18, 10-90% CH$_3$CN: water gradient over 45 minutes). Fractions containing the desired peptide were lyophilized, and confirmed using electrospray ionization mass spectrometry (ESI-MS) and NMR.

Figure 15B:
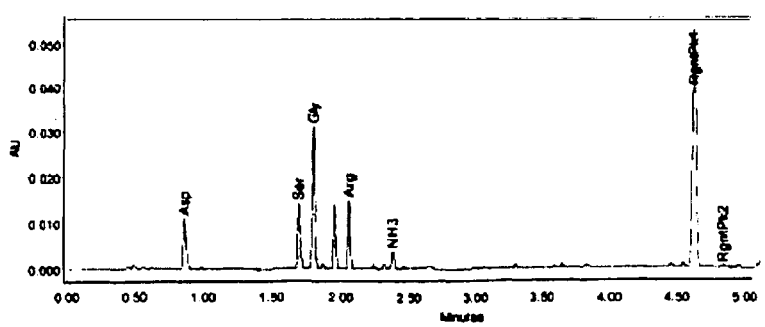

Conjugation of RGD peptide (6) to sulfhydryl-MC (5) was achieved by dissolving 5 in a solution of 0.1 M PBS buffer (pH 7.2) which was previously purged with N$_2$ gas for 20 minutes. Peptide 6 was then added and the reaction was stirred overnight at room temperature. Unreacted peptides were removed by extensive dialysis against 0.05 M PBS buffer (pH 7.0) for 2 days, followed by with DI water for another 2 days. Peptide-conjugated-MC (7) was then lyophilized to afford an amorphous white solid. Amino acid analysis determined the amount of peptide present in 7 to be 256 nmol peptide/mg of 7±22 nmol/mg, FIG. 15 B.

Those skilled in the art will appreciate that numerous changes and modifications can be made to this disclosure and that such changes and modifications can be made without departing from the spirit of the disclosure. It is, therefore, intended that the appended claims cover all such equivalent variations as fall within the true spirit and scope of the disclosure. The foregoing is illustrative of the present disclosure and is not to be construed as limiting thereof.

The invention claimed is:
1. An injectable cell delivery composition comprising as a cell delivery vehicle a polymer composition comprising:
  i) at least one thermal gelling polymer;
  ii) at least one anionic gelling polymer; and iii) a water-based carrier, wherein the polymer composition is injectable due to its shear thinning properties, the viscosity and network density of said polymer composition being effective to promote cell survival in vivo and in vitro and to maintain a distribution of cells after injection; and
at least one cell type for delivery selected from the group consisting of mammalian cells, stem cells, precursor and progenitor cell populations isolated from the adult neural subventricular zone, hippocampal subgranular zone, spinal cord, skin-derived precursors or adult retinal ciliary epithelium and their undifferentiated and differentiated progeny; embryonic stem cells and their undifferentiated and differentiated progeny; epiblast stem cells and their undifferentiated and differentiated progeny; primitive and definitive neural stem cells and their undifferentiated and differentiated progeny; induced pluripotent stem cells and their undifferentiated and differentiated progeny; mesenchymal stem cells and their undifferentiated and differentiated progeny; bone-marrow derived stem cells and their undifferentiated and differentiated progeny; hematopoietic stem cells and their undifferentiated and differentiated progeny; umbilical cord derived stem/progenitor cells and their undifferentiated and differentiated progeny; neural precursor cells of the forebrain, midbrain, hindbrain, spinal cord, neural crest, and retinal precursors isolated from developing tissue and their undifferentiated and differentiated progeny; and at least one factor capable of stimulating endogenous stem cells when present.

2. The injectable cell delivery composition as claimed in claim 1, wherein the thermal gelling polymer has a molecular weight between about 2,000 Da and about 1,000,000 Da and the anionic gelling polymer has a molecular weight between about 100,000 and about 7,000,000 Da and the ratio of the gelling polymer to the anionic polymer is at least about 0.1:1 to about 20:1 w/w.

3. The injectable cell delivery composition as claimed in claim 2, wherein the thermal gelling polymer is an inverse thermal gelling polymer selected from methylcellulose, a chitosan and beta-glycerophosphate solution, collagen, tri-block copolymer of poly(ethylene glycol)-poly(lactic-co-glycolic acid)-poly(ethylene glycol), tri-block copolymer of poly(propylene glycol)-poly(ethylene glycol)-poly(propylene glycol), poly(N-isopropyl acrylamide), agarose, copolymers of poly-N-isopropylacrylamide, polysaccharides and mixtures thereof; and the anionic gelling polymer is selected from: hyaluronic acid, derivatives of hyaluronic acid, alginate, derivatives of alginate, carboxymethylcellulose, and mixtures thereof.

4. The injectable cell delivery composition as claimed in claim 1, wherein the thermal gelling polymer is methylcellulose (MC) and the anionic gelling polymer is hyaluronic acid (HA).

5. The injectable cell delivery composition as claimed in claim 1, wherein the polymer composition is comprised of about 0.5% w/w methylcellulose and about 0.5% w/w hyaluronic acid.

6. The injectable cell delivery composition as claimed in claim 1, wherein the water-based carrier is selected from the group comprising: water, salt solutions, artificial cerebrospinal fluid, media, and buffered solutions.

7. The injectable cell delivery composition as claimed in claim 5, wherein the water-based carrier is selected from the group comprising: water, salt solutions, artificial cerebrospinal fluid, media, and buffered solutions.

8. The injectable cell delivery composition as claimed in claim 1, in a form for injection selected from the group consisting of subcutaneous, intramuscular and intravenous for delivery to a cavity in a patient creating surgically for therapeutic intervention or resulting from disease or injury.

9. The injectable cell delivery composition as claimed in claim 7, in a form for injection selected from the group consisting of subcutaneous, intramuscular and intravenous for delivery to a cavity in a patient creating surgically for therapeutic intervention or resulting from disease or injury.

10. The injectable cell delivery composition as claimed in claim 1, wherein the cells are delivered as spheres, aggregates or single cell suspensions.

11. The injectable cell delivery composition as claimed in claim 9, wherein the cells are delivered as spheres, aggregates or single cell suspensions.

12. The injectable cell delivery composition as claimed in claim 1, wherein at least one pharmaceutical agent is also present selected from the group comprising anesthetics for use in caudal, epidural, inhalation, injectable, retrobulbar, and spinal applications; analgesics, selected from the group comprising acetaminophen, ibuprofen, fluriprofen, ketoprofen, voltaren, phenacetin and salicylamide; anti-inflammatories selected from the group comprising naproxen and indomethacin; antihistamines, selected from the group comprising chlopheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussives selected from the group comprising dextromethorphan hydrobromide and guaifenesin; expectorants; decongestants, selected from the group comprising phenylephrine hydrochloride, phenylpropanolamine hydrochloride, pseudoephedrine hydrochloride, and ephedrine; antibiotics selected from the group comprising amebicides, broad and medium spectrum, fungal medications, monobactams and viral agents; bronchodilators selected from the group comprising theophylline, albuterol and terbutaline; cardiovascular preparations selected from the group comprising diltiazem, propranolol, nifedepine, clonidine, alpha adrenoceptor agonists, alpha receptor blocking agents, alpha and beta receptor blocking agents, antiotensin converting enzyme inhibitors, beta blocking agents, calcium channel blockers, and cardiac glycosides; central nervous system drugs selected from the group comprising thioridazine, diazepam, meclizine, ergoloid mesylates, chlorpromazine, carbidopa and levodopa; metal salts selected from the group comprising potassium chloride and lithium carbonate; minerals selected from the group consisting of iron, chromium, molybdenum and potassium; immunomodulators; immunosuppressives selected from the group comprising minocycline, cyclosporine A; thyroid preparations selected from the group comprising synthetic thyroid hormone, and thyroxine sodium; peptide and glycoprotein hormones and analogues selected from the group comprising human chorionic gonadotrophin (HCG), corticotrophin, human growth hormone (HGH~Somatotrophin) and erythropoietin (EPO); steroids and hormones selected from the group comprising ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, and GM1 ganglioside; small molecules, including taurine, retinoic acid, sodium butyrate, cAMP, dbcAMP; vitamins selected from the group comprising water-soluble vitamins and veterinary formulations; growth factors, proliferative factors, differentiation factors and morphogens selected from the group comprising EGF, FGF2, EPO, PDGF-AA, BDNF, GDNF, SHH, IFN-γ and neurotrophins; peptides, peptide mimetics and other protein preparations; anti-angiogenics selected from the group comprising, but not limited to, ranibizumab, bevacizumab, and pegaptanib; DNA; and, small interfering RNAs; and when required a pharmaceutically acceptable carrier or preservative; and at least one factor capable of stimulating endogenous stem cells is present.

13. The injectable cell delivery composition as claimed in claim 12, wherein the at least one pharmaceutical agent is covalently bonded to at least one of the thermal gelling polymer and the anionic gelling polymer.

14. The injectable cell delivery composition as claimed in claim 12, wherein the at least one pharmaceutical agent is encapsulated in a micron-sized particle or nanoparticle selected from microspheres, micron-sized rods, nanospheres, nanorods and liposomes; and the micron-sized particles that incorporate the pharmaceutical agents are dispersed in the polymer along with the cells prior to injection to ensure an even distribution of cells and microspheres.

15. The injectable cell delivery composition as claimed in claim 4, wherein the ratio of MC to HA is about 0.1:1 to about 5:1 w/w.

16. The injectable cell delivery composition as claimed in claim 15, wherein the concentration of MC is from 0.5 wt. % to 1.0 wt. % and the concentration of HA is from 0.5 wt. % to 1.0 wt. %.

* * * * *